(12) United States Patent
Giacalone

(10) Patent No.: US 11,167,008 B2
(45) Date of Patent: Nov. 9, 2021

(54) IMMUNOMODULATORY AND ONCOLYTIC MINICELLS AND METHODS OF USE

(71) Applicant: Vaxiion Therapeutics, LLC, San Diego, CA (US)

(72) Inventor: Matthew J. Giacalone, San Diego, CA (US)

(73) Assignee: VAXIION THERAPEUTICS, LLC, San Diego, CA (US)

( * ) Notice: Subject to any disclaimer, the term of this patent is extended or adjusted under 35 U.S.C. 154(b) by 6 days.

(21) Appl. No.: 15/820,063

(22) Filed: Nov. 21, 2017

(65) Prior Publication Data

US 2018/0140665 A1 May 24, 2018

Related U.S. Application Data

(60) Provisional application No. 62/426,066, filed on Nov. 23, 2016.

(51) Int. Cl.

| *A61K 45/06* | (2006.01) |
|---|---|
| *A61K 38/16* | (2006.01) |
| *A61K 39/395* | (2006.01) |
| *C07K 16/28* | (2006.01) |
| *A61K 39/02* | (2006.01) |
| *A61K 39/39* | (2006.01) |
| *A61K 39/00* | (2006.01) |
| *A61K 35/74* | (2015.01) |

(52) U.S. Cl.
CPC ........ *A61K 38/164* (2013.01); *A61K 39/0291* (2013.01); *A61K 39/39* (2013.01); *A61K 39/39558* (2013.01); *A61K 45/06* (2013.01); *C07K 16/2827* (2013.01); *A61K 35/74* (2013.01); *A61K 2039/505* (2013.01); *A61K 2039/54* (2013.01); *A61K 2039/545* (2013.01); *A61K 2039/55555* (2013.01); *A61K 2039/585* (2013.01); *C07K 2317/76* (2013.01)

(58) Field of Classification Search
CPC ............ A61K 38/164; A61K 39/39558; A61K 45/06; C07K 16/2827
USPC ..................................................... 424/174.1
See application file for complete search history.

(56) References Cited

U.S. PATENT DOCUMENTS

| 4,895,724 A | 1/1990 | Cardinal et al. |
|---|---|---|
| 5,314,695 A | 5/1994 | Brown |
| 7,183,105 B2 | 2/2007 | Sabbadini et al. |
| 7,396,822 B2 | 7/2008 | Sabbadini et al. |
| 8,691,963 B2 | 4/2014 | Brahmbhatt et al. |
| 8,772,013 B2 | 7/2014 | Brahmbhatt et al. |
| 9,169,495 B2 | 10/2015 | Brahmbhatt et al. |
| 9,267,108 B2 | 2/2016 | Giacalone |
| 9,566,321 B2 * | 2/2017 | Giacalone .............. C07K 14/33 |
| 10,039,817 B2 * | 8/2018 | Giacalone .............. C07K 14/33 |
| 2010/0112670 A1 | 5/2010 | Giacalone et al. |
| 2012/0207754 A1 | 8/2012 | Giacalone et al. |

FOREIGN PATENT DOCUMENTS

| WO | WO1998/52547 | 11/1998 |
|---|---|---|
| WO | WO 2014/055682 | 4/2014 |
| WO | WO2017/024059 | 2/2017 |

OTHER PUBLICATIONS

MacDiarmid, et al., "Bacterially Derived 400 nm Particles for Encapsulation and Cancer Cell Targeting of Chemotherapeutics" Cancer Cell, 2007, vol. 11, p. 431-445.
International Search Report and the Written Opinion dated Mar. 9, 2018 in PCT/US2017/062814, filed Nov. 21, 2017.
Tsuji, et al., "Preclinical evaluation of VAX-IP, a novel bacterial minicell-based biopharmaceutical for nonmuscle invasive bladder cancer", Molecular Therapy—Oncolytics, vol. 3, Jan. 1, 2016, pp. 2-13.
Ghasemzadeh, et al., "New Strategies in Bladder Cancer: A Second Coming for Immunotherapy" Clin Cancer Res; 22(4), Feb. 15, 2016, pp. 793-801.

\* cited by examiner

*Primary Examiner* — Yan Xiao
(74) *Attorney, Agent, or Firm* — Knobbe, Martens, Olson & Bear LLP

(57) ABSTRACT

Disclosed herein are compositions comprising immunomodulatory and oncolytic eubacterial minicells, and the use of the composition in immunomodulatory therapies for cancer. In some embodiments, the minicells are used in combination of immune checkpoint inhibitors in treating cancer.

20 Claims, 3 Drawing Sheets

IMMUNOMODULATORY AND ONCOLYTIC MINICELLS AND METHODS OF USE

CROSS-REFERENCE TO RELATED APPLICATIONS

This application claims the benefits of U.S. Provisional Patent Application No. 62/426,066 filed on Nov. 23, 2016, the content of which is hereby incorporated by reference in its entirety.

BACKGROUND

Field

The present application is drawn to compositions and methods for the production, purification, formulation, and use of immunomodulatory, immunotherapeutic, and oncolytic eubacterial minicells for use as single agent therapeutics and in synergistic combination with other immunotherapies in cancer.

Description of the Related Art

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Recent cancer immunotherapy research has focused substantial effort on approaches that enhance anti-tumor immunity by adoptive-transfer of activated effector cells, immunization against relevant antigens, providing non-specific immune-stimulatory agents such as cytokines, or removing inhibitors to anti-cancer effector cells. Immune checkpoint inhibitors have been developed to provide new immunotherapeutic approaches for treating cancer. Since cancer remains as an incurable disease for the great majority of patients, there is a need for developing effective therapeutic agents that can be used in cancer immunotherapy.

SUMMARY

Some embodiments disclosed herein provide a method of treating a subject with bacterial minicells, preferably oncolytic bacterial minicells, in combination with an immune checkpoint inhibitor therapy to provide synergistic benefit to the subject as mediated by the ability of this combination to activate an anti-tumor immune response that results in protective, durable, anti-tumor immunological memory.

Methods for treating cancer are provided herein. In some embodiments, the method comprising administering a first pharmaceutical composition comprising bacterial minicells and a second pharmaceutical composition comprising one or more immune checkpoint inhibitors to a subject with cancer. In some embodiments, the first pharmaceutical composition comprises D-trehalose. In some embodiments, the first and second pharmaceutical compositions are administered to the subject simultaneously. In some embodiments, the first and second pharmaceutical compositions are administered to the subject sequentially. For example, the first pharmaceutical composition can be administered to the subject before and/or after the second pharmaceutical composition is administered to the subject.

The first pharmaceutical composition can be administered to the subject via various routes, for example via oral, intravenous, intraperitoneal, intragastric, intravesical administration, or a combination thereof. The second pharmaceutical composition can also be administered to the subject via various routes, for example via oral, intravenous, intraperitoneal, intragastric, intravesical administration, or a combination thereof. In some embodiments, the first pharmaceutical composition is administered to the subject at least twice. In some embodiments, the second pharmaceutical composition is administered to the subject at least twice. In some embodiments, the first and/or the second pharmaceutical composition comprises one or more pharmaceutically acceptable excipients.

In some embodiments, the method further comprises administering one or more additional chemotherapeutic agents to the subject. In some embodiments, at least one of the one or more additional chemotherapeutic agents is administered to the subject separately from the first and or the second compositions. In some embodiments, the bacterial minicells comprise invasin or a functional fragment thereof. In some embodiments, the bacterial minicells comprise perfringolysin O (PFO) or a functional fragment thereof. In some embodiments, the bacterial minicells do not comprise any exogenous protein toxin other than PFO. In some embodiments, the bacterial minicells do not comprise any exogenous therapeutic compounds or exogenous therapeutic protein other than PFO.

In some embodiments, the cancer is a solid tumor or hematological cancer. In some embodiments, at least one of the one or more immune checkpoint inhibitors is selected from the group consisting of inhibitors of PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, KIR, and any combinations thereof. In some embodiments, at least one of the one or more immune checkpoint inhibitors is selected from the group consisting of antibodies of PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, KIR, and any combinations thereof.

BRIEF DESCRIPTION OF THE DRAWINGS

As shown in FIG. 1, immunocompetent mice bearing orthotopic bladder tumors who survive intravesical treatment with oncolytic VAX014 minicells are able to reject a second round of the same orthotopic bladder tumor type (89% rejected a second tumor installation).

DETAILED DESCRIPTION

Definitions

Figure 1:
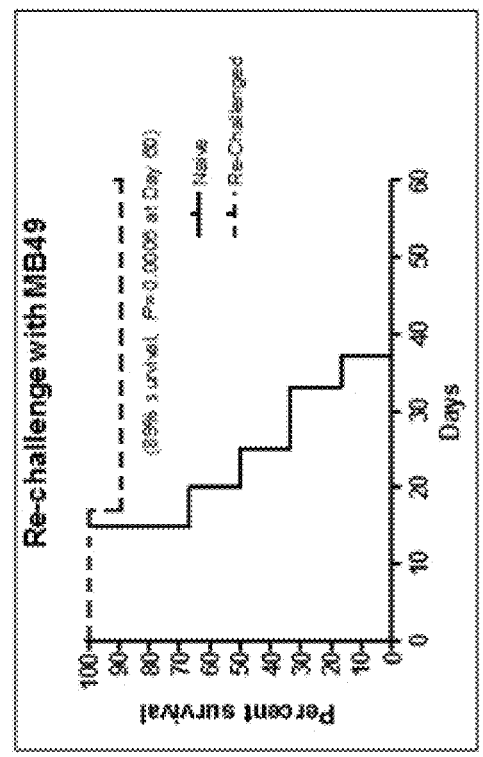
FIG. 1 shows percent survival of animals after MB49 early treatment and re-challenge with MB49.
Figure 1:
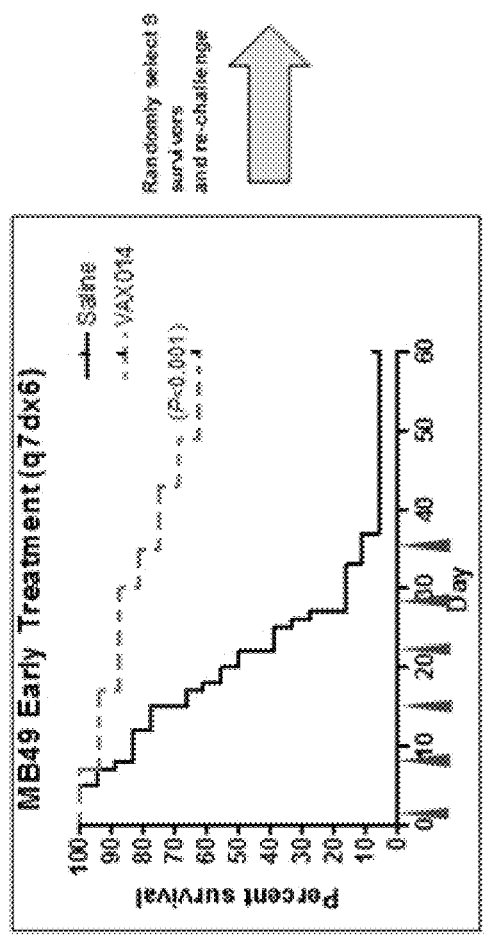

As used herein, the term "Th1 immunomodulatory minicells" refers to minicells that are capable of stimulating a Th1 innate immune response.

As used herein, the term "Th2 immunomodulatory minicells" refers to minicells that are capable of stimulating a Th2 innate immune response.

As used herein, the term "Th1/Th2 immunomodulatory minicells" refers to minicells that are capable of stimulating both a Th1 and Th2 innate immune response.

As used herein, the term "recombinant invasive immunomodulatory minicell" refers to a minicell that has been genetically engineered to express and display heterologous minicell surface proteins capable of stimulating internalization into eukaryotic cells.

As used herein, the term "naturally invasive immunomodulatory minicell" refers to a minicell produced from a normally invasive bacterium such that said minicells express and display naturally occurring minicell surface proteins capable of stimulating internalization into eukaryotic cells.

As used herein, the term "immunomodulatory" refers to the modulation of the immune response in a desired fashion, including but not limited to, the production of innate Th1 and innate Th2 immune responses.

As used herein, the term "immunotherapy" refers to the use of an immunomodulatory compound, preferably an immunomodulatory oncolytic minicell, to generate an innate and/or adaptive immune response that has beneficial effect with respect to the elimination or slowing the progression of disease, especially cancer.

As used herein, the term "adherent minicell" refers to a minicell that is capable of binding and adhering to the surface of a non-constitutively phagocytic eukaryotic cell without stimulating appreciable endocytosis of said minicells.

As used herein, the term "muco-adherent minicell" refers to a minicell that is capable of binding and adhering to a mucosal surface.

As used herein, the term "oncolytic minicell" refers to a minicell that is capable of stimulating direct tumor cell lysis. Oncolytic minicells are also capable of indirectly activating the immune system during, or shortly after direct oncolytic effects are exerted, eliciting in situ vaccination against tumors when administered to a subject suffering from cancer.

As used herein, the term "integrin targeted minicells" refers to minicells that express and display the pan-Beta1-integrin-targeting cell surface molecule Invasin from *Yersinia pseudotuberculosis* or any functional equivalents thereof. Integrin targeted minicells are also defined as those minicells that comprise a surface-localized integrin-specific antibody or antibody derivative.

As used herein, the term "VAX-IP minicells" refers to minicells that express and display the pan-Beta1-integrin-targeting cell surface molecule Invasin from *Yersinia pseudotuberculosis* and any functional equivalents thereof wherein the minicells comprise perfringolysin O (PFO).

As used herein, the term "VAX014 minicells", synonymous with "VAX014", refers to a sterile formulation of VAX-IP minicells wherein D-trehalose is used as an excipient. VAX014 minicells can be formulated in various formulations, for example, as a freeze-dried lyophile or as a suspension.

As used herein, the term "invasin target integrin" refers to any mammalian beta1 integrin heterodimer capable of being bound by invasin.

As used herein, the term "prokaryotic cell division gene" refers to a gene that encodes a gene product that participates in the prokaryotic cell division process. Many cell division genes have been discovered and characterized in the art. Examples of cell division genes include, but are not limited to, zipA, sulA, secA, dicA, dicB, dicC, dicF, ftsA, ftsI, ftsN, ftsK, ftsL, ftsQ, ftsW, ftsZ, minC, minD, minE, seqA, ccdB, sfiC, and ddlB.

As used herein, the term "transgene" refers to a gene or genetic material that has been transferred naturally or by any of a number of genetic engineering techniques from one organism to another. In some embodiments, the transgene is a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In some embodiments, the transgene is an artificially constructed DNA sequence, regardless of whether it contains a gene coding sequence, which is introduced into an organism in which the transgene was previously not found.

As used herein, an agent is said to have been "purified" if its concentration is increased, and/or the concentration of one or more undesirable contaminants is decreased, in a composition relative to the composition from which the agent has been purified. In some embodiments, purification includes enrichment of an agent in a composition and/or isolation of an agent therefrom.

The term "sufficiently devoid of parental cells", synonymous with "sufficiently devoid", as used herein refers to a composition of purified minicells that have a parental cell contamination level that has little or no effect on the toxicity profile and/or therapeutic effect of targeted therapeutic minicells. In some embodiments, a composition of minicells that is sufficiently devoid of parent cells contains no more than 5%, 4%, 3%, 2%, 1%, or less parent cells.

The term "domain" or "protein domain" used herein refers to a region of a molecule or structure that shares common physical and/or chemical features. Non-limiting examples of protein domains include hydrophobic transmembrane or peripheral membrane binding regions, globular enzymatic or receptor regions, protein-protein interaction domains, and/or nucleic acid binding domains.

The terms "Eubacteria" and "prokaryote" are used herein as these terms are used by those in the art. The terms "eubacterial" and "prokaryotic" used herein encompass Eubacteria, including both Gram-negative and Gram-positive bacteria, prokaryotic viruses (e.g., bacteriophage), and obligate intracellular parasites (e.g., Richettsia, Chlamydia, etc.).

The term "immunopotentiating polypeptide" is synonymous with "immunostimulatory polypeptide", "immunomodulatory polypeptide", and "immunotherapeutic polypeptide" and the terms are used interchangeably herein to refer to any collection of diverse protein molecule types that have an immunomodulatory/immunotherapeutic effect when introduced into a eukaryotic organism or cell (e.g., a mammal such as human). An immunomodulatory polypeptide can be a cytokine, a chemokine, a functional enzyme, an antibody or antibody mimetic, an activated caspase, a procaspase, a cell-penetrating peptide, or any combination and/or plurality of the proceeding. The term should not be confused with the word "immunogen" or "antigen", each of which is described below.

The term "oncolytic polypeptide" is synonymous with "tumorlytic polypeptide" and the terms are used interchangeably herein to refer to any protein that has a lytic effect when introduced into a eukaryotic organism or cell (e.g., a mammal such as a human). An oncolytic polypeptide can include, but is not limited to, a cholesterol-dependent cytolysin, a phospholipase, a functional enzyme, a cell-penetrating peptide, a perforin, or any combination thereof.

The terms "immunogen" and "antigen" are interchangeable and used herein to refer to polypeptides, carbohydrates, lipids, nucleic acids, and other molecules to which an antigen-specific antibody, cellular, and/or allergenic response may be mounted against. Antigen-specific immune responses shall rely on the presence of the antigen/immunogen, and shall not be included in the definition of Th1 or Th2 immunomodulatory responses as used herein.

The terms "neo-antigen" and "neo-immunogen" are interchangeable and used herein to refer to tumor selective polypeptides, carbohydrates, lipids, nucleic acids, and other molecules to which an antigen-specific antibody, cellular, and/or allergenic response may be mounted against. Neo-antigens can arise from tumor-cell specific mutations in self-proteins and may be derived from chromosomally encoded mutations that change the natural amino acid sequence of the corresponding wild type protein or mutations that impact the mRNA in non-coding regions such that improper mRNA splicing leads to new protein sequences. Neo-antigen-specific immune responses shall rely on the presence of the neo-antigen/neo-immunogen in the context of cancer, and shall not be included in the definition of Th1 or Th2 immunomodulatory responses as used herein.

The terms "personalized neo-antigen" and "personalized neo-immunogen" are used interchangeably herein to refer to patient-specific tumor-selective polypeptides, carbohydrates, lipids, nucleic acids, and other molecules to which an antigen-specific antibody, cellular, and/or allergenic response may be mounted against. Personalized neo-antigens are identified from patient-specific tumor samples using various sequencing methods know in the art.

The terms "personalized neo-antigen vaccine" and "personalized neo-immunogen vaccine" are used interchangeably herein to refer to a polypeptide-based vaccine based on one or more patient-specific tumor-selective polypeptides identified from patient-specific tumor samples using various sequencing methods know in the art. Such personalized neo-antigen vaccines may be synthetically or recombinantly derived and may be administered as individual peptide sequences or as a single contiguous polypeptide, commonly referred to a "string-of-beads vaccine" approach in the art. Contiguous personalized neoantigen sequences may contain spacer/linker polypeptide sequences to optimize cleavage and major histocompatibility complex loading. Personalized neo-antigen vaccines may be delivered by bacterial minicells or oncolytic bacterial minicells as recombinant proteins.

The term "in situ vaccination" used herein refers to the development of adaptive anti-tumor immunological responses, preferably memory responses, elicited in vivo after administration of and exposure of tumors to minicells, preferably oncolytic minicells. The in situ vaccination effect is a result of the release of tumor selective antigens and neo-antigens into the extracellular milieu, an effect mediated by oncolysis.

The term "overexpression" used herein refers to the expression of a functional nucleic acid, polypeptide or protein encoded by DNA in a host cell, wherein the nucleic acid, polypeptide or protein is either not normally present in the host cell, or wherein the nucleic acid, polypeptide or protein is present in the host cell at a higher level than that normally expressed from the endogenous gene encoding the nucleic acid, polypeptide or protein.

The term "modulate" as used herein means to interact with a target either directly or indirectly so as to alter the activity of the target to regulate a biological process. The meaning of "modulate" includes, but is not limited to, enhancing the activity of the target, inhibiting the activity of the target, limiting the activity of the target, and extending the activity of the target.

The term "heterologous" as used herein refers to a protein(s), gene(s), nucleic acid(s), imaging agent(s), buffer component(s), or any other biologically active or inactive material that is not naturally found in a minicell or minicell-producing bacterial strain, and is introduced and expressed, transcribed, translated, amplified or otherwise generated by minicell-producing bacterial strains that harbor recombinant genetic material coding for said heterologous material or coding for genes that are capable of producing said heterologous material (e.g., a bioactive metabolite not native to the parent cell).

The term "exogenous" as used herein refers to a protein(s) (including antibodies), gene(s), nucleic acid(s), small molecule drug(s), imaging agent(s), buffer(s), radionuclide(s), or any other biologically active or inactive material that is not native to a cell, or in the case of a minicell, not native to the parent cell of the minicell. Exogenous material differs from heterologous material by virtue of being derived, generated, purified, and/or added separately.

The term "therapeutic" as used herein means having a biological effect or combination of biological effects that prevents, inhibits, eliminates, cures, or prevents progression of a disease or other aberrant biological processes in an animal.

The term "diagnostic" as used herein means having the ability to detect, monitor, follow, and/or identify a disease or condition in an animal (including humans) or from a biological sample including but not limited to blood, urine, saliva, sweat and fecal matter.

The term "theranostic" as used herein means having the combined effects of a therapeutic and a diagnostic composition.

The term "recombinantly expressed" as used herein means the expression of one or more nucleic acid(s) and/or protein(s) from a nucleic acid molecule that is artificially constructed using modern genetic engineering techniques wherein the artificially constructed nucleic acid molecule does not occur naturally in minicells and/or minicell-producing bacterial strains wherein the artificial nucleic acid molecule is present as an episomal nucleic acid molecule or as part of the minicell-producing bacterial chromosome.

The term "episomal" as used herein means a nucleic acid molecule that is independent of the chromosome(s) of a given organism or cell.

The term "detoxified" as used herein refers to a modification made to a composition or component thereof that results in a significant reduction in acute toxicity to the modified composition or component thereof, regardless of what the causative biological basis for toxicity to the composition or component thereof happens to be.

As used herein, the term "bioactive molecule" refers to a molecule having a biological effect on a eukaryotic organism or cell (e.g., a mammal such as a human) when introduced into the eukaryotic organism or cell. Bioactive molecules include, but are not limited to, therapeutic nucleic acids, therapeutic polypeptides (for example, protein toxins), and therapeutic small molecule drugs.

As used herein, the term "subject" refers to a human or a non-human mammal, e.g., a dog, a cat, a mouse, a rat, a cow, a sheep, a pig, a goat, a non-human primate, or a bird, e.g., a chicken, as well as any other vertebrate or invertebrate. The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice, guinea pigs, and the like.

An "effective amount" or a "therapeutically effective amount" as used herein refers to an amount of a therapeutic agent that is effective in its purpose to impart therapeutic benefit, which includes but is not limited to the relief, reduction, delayed onset, and cure of one or more of the symptoms of a disease or condition, and can include curing, stabilizing, and managing a disease or condition.

The terms "treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Description

The present application relates to the use of bacterial minicells in vivo to stimulate the immune system in such a way as to generate a tumor cell-specific anticancer effect. The minicells of the present disclosure include, but are not limited to, oncolytic minicells, which are capable of enhanced tumor selective lysis. Direct tumor lysis, "oncolysis", leads to tumor neo-antigen release, where they may be recognized by the immune system. The inherent immunostimulatory adjuvant activity of bacterial minicells then helps to drive and sustain both innate and adaptive immune recognition of these neo-antigens, ultimately leading to the development of adaptive tumor-specific immune responses that mediate tumor killing and tumor-specific adaptive immunological memory responses in a process commonly referred to as "in situ vaccination". Minicells and oncolytic minicells used in the context of the present disclosure can be combined with immune checkpoint inhibitor therapies. The combination of oncolytic minicell-mediated tumor neo-antigen exposure and adjuvant properties with the T-cell activation properties of immune checkpoint inhibitors synergize to improve anti-tumor immune responses, including but not limited to T-cell and NK-cell mediated cytotoxic lymphocyte (CTL) responses against tumors. The effectiveness of this combination therapy can be enhanced by further combination with other treatment modalities known to aid in neo-antigen exposure (e.g. co-delivery of a personalized neo-antigen vaccine), immune cell activation, epigenetic modulation, anti-metabolite activity, and proteasome inhibition. In the case of combination of an oncolytic minicell with a personalized neo-antigen vaccine, said personalized neo-antigen vaccine may be delivered within the context of the oncolytic minicell (i.e. the minicell contains both an oncolytic polypeptide and a second polypeptide as the personalized neo-antigen vaccine).

Bacterial minicells are achromosomal, membrane-encapsulated biological nanoparticles (approximately 250-500 nm in diameter) that are formed by bacteria following disruption of the normal division process of bacterial cells. In essence, minicells are small replicas of normal bacterial cells with the exception that they contain no chromosomal DNA and as such, are non-dividing, non-viable, and non-infectious. Bacterial minicells are minimally metabolically active when purified from parental bacterial cells. What little metabolic activity minicells do have is finite, and quickly diminishes below detectable/functional levels following purification. Although minicells do not contain bacterial chromosomes, plasmid DNA molecules (smaller than chromosomes), RNA molecules (of all subtypes and structures), native and/or recombinantly expressed proteins, and other metabolites have all been shown to segregate into minicells during the budding process. As such, minicells are uniquely suited as in vivo delivery vehicles because they can be engineered to combine one or more different naturally occurring, heterologous, or exogenous molecular components into a single particle, where each component is present in discreet amounts. This is in stark contrast to live bacterial-based delivery vehicles where live bacteria are capable of division and persistence, while generating unknown quantities of molecular components de novo after administration in vivo. Persistence and propagation of living bacterial delivery vehicles can lead to many different complications including infection, organ failure, sepsis, and death. In short, minicells can be "engineered" to preferentially encapsulate, be coupled to, or absorb biologically active molecules, including various nucleic acids, proteins, small molecule drugs, and any combination thereof for subsequent generation of biological responses in both prophylactic and therapeutic medicinal applications where the prevention, maintenance, and/or inhibition of disease by way of said biologic response is desirable.

Genetically engineered bacterial minicells have been used directly as anti-cancer agents as described in U.S. Pat. No. 7,183,105, which is incorporated herein by reference in its entirety. For example, it has been taught within U.S. Pat. No. 7,183,105 that minicells can be engineered to use minicell surface-localized antibodies to target and deliver small molecule drugs, peptides, proteins, and various nucleic acids, together or in concert directly to cancer cells to exert a direct targeted anticancer effect. Other investigators have also reported the same findings as those taught in U.S. Pat. No. 7,183,105, with respect to the use of minicells as targeted delivery vehicles, as illustrated in U.S. Pat. Nos. 8,691,963, 8,772,013, and 9,169,495, each of which is incorporated herein by way of reference. Also, U.S. Pat. No. 9,267,108 teach that minicells can be engineered and utilized as anti-cancer therapies capable of exerting indirect and non-selective anti-tumor effects. The references teach the same approach to using minicells to specifically target and deliver anti-cancer agents directly to tumor cells in vivo, but not the use of bacterial minicells to cause tumor-specific immune activation in response to treatment with minicells or oncolytic minicells. Bacterial minicell-based compositions designed to generate tumor-specific adaptive immune responses are described in U.S. Pat. Nos. 7,183,105, 7,396, 822, and U.S. Patent Publication No. 2012-0207754 in the context of using the bacterial minicell as a carrier of a recombinant tumor selective antigen (e.g., a tumor selective single antigen "cancer vaccine"). In U.S. Pat. Nos. 8,691, 963, 8,772,013, and 9,169,495, it shows that targeting, using an antibody selective for a known tumor selective cell surface receptor coupled to the surface of the minicell vehicle is required for anti-tumor activity. Further, these references also indicate that when non-targeted minicells are used, that no significant anti-tumor response is observed. In other related work, MacDiarmid and colleagues demonstrate that both non-targeted minicells and tumor-targeted minicells containing no cytotoxic drug payload, are equally incapable of generating an anti-tumor response and that both a targeting antibody and the cytotoxic payload are required for activity (MacDiarmid, et al. *Cancer Cell,* 2007, Volume 11, p. 431-445). Additionally, the authors of this work claim the benefits of evading the immune system, describe this desired feature as part of their rationale for design, and therefore explicitly teach away from using minicells as immunomodulatory therapeutics. None of the prior art references describe the use of bacterial minicells (for example oncolytic minicells) in combination with immune checkpoint inhibitor(s).

In contrast to the prior art, the present disclosure is drawn to the use of bacterial minicells (for example, oncolytic bacterial minicells) as therapeutics capable of eliciting tumor-specific immune responses in vivo. In some embodiments, the present disclosure is drawn to the use of oncolytic bacterial minicells as therapeutics capable of eliciting potent anti-tumor effects by simultaneous tumor-selective killing and enhanced neo-antigen exposure resulting from minicell-mediated tumor cell lysis. Thus, disclosed herein are compositions and methods for killing tumor cells and/or tumor endothelial cells by a first direct mechanism followed by a second mechanism wherein said first mechanism is a direct cytotoxic lytic mechanism mediated by minicell-based targeted delivery of a lytic polypeptide and where said second mechanism depends from the first mechanism to stimulate, propagate and sustain an anti-tumor immune response. In some embodiments, the lysis results in tumor cell antigen release, including but not limited to, neoantigen release, ultimately resulting in immune recognition and immune activation that leads to immune-mediated selective killing of said tumor. In some embodiments, bacterial minicells, including but not limited to oncolytic bacterial minicells, are used in combination with one or more immune checkpoint inhibitors. Said immune checkpoint inhibitors include those against either or both of co-stimulatory or inhibitory checkpoints and specifically include, but are not limited to, those inhibitors against PD-1, PD-L1, PD-L2, CTLA-4, LAG-3, IDO, GITR, 4-1BB, OX40, CD27, KIR2DL, CSF1R, CD40L, and TIM-3.

In some embodiments, minicells (for example, oncolytic minicells) are engineered to express one or more recombinant tumor-selective antigens to bolster the overall amount of tumor selective antigen(s) released in response to minicell treatment. Recombinant tumor-selective antigens utilized in the context of these embodiments of the disclosure include, but are not limited to, HER-2, K-RAS, H-RAS, N-RAS, MAGE, c-MYC, MUC-1, PSMA, CEA, ETA, CA-125, p53, AFP, Tyrosinase, and any of oncofetal proteins, antigens produced by oncogenic viruses, and products of mutated genes (i.e. neo-antigens). Further, the embodiments can, for example, include the incorporation of patient derived and patient-specific personalized neo-antigens, whereby a patient suffering from cancer has a unique genomic signature from which personalized neo-antigenic sequences may be derived via in silico technologies and algorithms known in the art. A DNA sequence for said personalized neo-antigens is then generated and cloned into a prokaryotic expression vector prior to being introduced into a minicell-producing bacterial strain where it is recombinantly expressed and becomes the neo-antigen component of a bacterial minicell or oncolytic bacterial minicell prior to administration to the patient. Bacterial minicells further comprising recombinantly expressed tumor antigens and patient-specific personalized neo-antigens, including but not limited to oncolytic bacterial minicells expressing the same, are used, in some embodiments, in combination with one or more immune checkpoint inhibitors. Said immune checkpoint inhibitors include those inhibitors against either or both of co-stimulatory or inhibitory checkpoints and specifically include, but are not limited to, those against PD-1, PD-L1, PD-L2, CTLA-4, LAG-3, IDO, GITR, 4-1BB, OX40, CD27, KIR2DL, CSF1R, CD40L, and TIM-3.

In some embodiments, minicells (for example, oncolytic minicells) comprising recombinant tumor selective antigens and personalized patient-specific neo-antigens or oncolytic bacterial minicells expressing the same are administered in combination with CAR-T or CAR-N autologous immune cell therapies. Recombinant tumor selective antigens utilized in the context of these embodiments of the disclosure include, but are not limited to, HER-2, K-RAS, H-RAS, N-RAS, MAGE, c-MYC, MUC-1, PSMA, CEA, ETA, CA-125, p53, AFP, Tyrosinase, and any of oncofetal proteins, antigens produced by oncogenic viruses, and products of mutated genes (i.e. neo-antigens). The CAR-T or CAR-N therapy expresses one or more chimeric antigen receptors specific for said tumor selective antigen. Further, these embodiments can include the incorporation of patient-derived and patient-specific neo-antigens, whereby a patient suffering from cancer has a unique genomic signature from which neo-antigenic sequences may be derived via in silico technologies and algorithms known in the art and then recombinantly expressed as the neo-antigen component of the bacterial minicell or oncolytic bacterial minicell prior to re-introduction into the patient followed by administration of CAR-T or CAR-N therapy specific for the same. Bacterial minicells further comprising recombinantly expressed tumor antigens and patient-specific personalized neo-antigens, including but not limited to oncolytic bacterial minicells expressing the same, and combined with CAR-T and CAR-N therapies, are used in further combination with one or more immune checkpoint inhibitors. Said immune checkpoint inhibitors include those inhibitors against either or both of co-stimulatory or inhibitory checkpoints and specifically include, but are not limited to, those against PD-1, PD-L1, PD-L2, CTLA-4, LAG-3, IDO, GITR, 4-1BB, OX40, CD27, KIR2DL, CSF1R, CD40L, and TIM-3.

In some embodiments, bacterial minicells (for example, oncolytic bacterial minicells) include, but are not limited to, those produced from naturally invasive strains of bacteria including but not limited to invasive strains of *Salmonella* spp., *Listeria* spp., *Mycobacterium* spp., *Shigella* spp., *Yersinia* spp., and *Escherichia coli*. These naturally invasive minicells and oncolytic minicells derived therefrom will display naturally occurring minicell surface-localized ligands capable of stimulating internalization of minicells into eukaryotic cells. It should be taken into consideration that naturally-invasive minicells do not exist in nature per se, but rather are engineered from non-minicell producing invasive strains of bacteria using one or more of the genetic approaches to generating minicells as described herein.

In some embodiments, minicells and oncolytic minicells include, but are not limited to, those produced from non-invasive strains of bacteria. Many non-invasive strains of bacteria are known to the skilled artisan and include, but are not limited to, non-invasive strains of *Escherichia coli, Salmonella* spp., *Shigella* spp., *Lactobacillus* spp., *Pseudomonas* spp., and the like.

In some embodiments, minicells (for example, oncolytic minicells) produced from non-invasive strains of bacteria, may be made invasive by including heterologous gene sequences encoding for surface-localized ligands from invasive bacterial species. Such ligands include, but are not limited to, bacterial adhesins, intimins, and invasins. Many non-invasive strains of bacteria that may be converted into invasive minicell-producing strains are known to the skilled artisan and include, but are not limited to, non-invasive strains of *Escherichia coli, Salmonella* spp., *Shigella* spp., *Lactobacillus* spp., *Pseudomonas* spp., and the like.

Minicells have distinct mechanisms and advantages with respect to loading of polypeptides (e.g., cytokines, protein toxins, cholesterol-dependent cytolysins, and personalize neo-antigens) and nucleic acids (e.g. circular double-stranded plasmid DNA, double-stranded RNA, single-stranded RNA, hairpin RNA, and double-stranded linear DNA). For example, immunomodulatory minicell-producing parental bacterial cells can be used to recombinantly express/produce one or more cytokines, protein toxins, and cytolysins prior to or while minicells are being produced. Recombinant polypeptides are expressed, segregate into, and are encapsulated by minicells, and then utilized to enhance, modulate, and/or stabilize innate or adaptive immune responses elicited by immunomodulatory minicells in vivo.

In cases where polypeptide(s) are pre-formed by the parental cell by way of recombinant expression from a prokaryotic expression cassette (either chromosomal or episomal in location) and is then packaged inside of the minicells as an oncolytic protein and/or tumor selective antigen, the half-life of the polypeptide(s) within the minicell is increased by use of minicell producing bacterial strains harboring one or more deletions or other non-functional mutations in protease genes (e.g., the lon protease of *E. coli*) responsible for proteolysis. In the absence of the protease(s), the protein toxin molecules accumulate to a higher level, increasing the potency of targeted minicells delivering the therapeutic polypeptide molecules. In the case of *Escherichia coli* minicell producing strains, mutation or deletions can be introduced into one or more of the lon, tonB, abgA, ampA, ampM, pepP, clpP, dcp, ddpX/vanX, elaD, frvX, gcp/b3064, hslV, hchA/b1967, hyaD, hybD, hycH, hycI, iadA, ldcA, ycbZ, pepD, pepE, pepQ, pepT, pmbA, pqqL, prlC, ptrB, sgcX, sprT, tldD, ycaL, yeaZ, yegQ, ygeY, yggG, yhbO, yibG, ydpF, degS, ftsH/hflB, glpG, hofD/hopD, lepB, lspA, pppA, sohB, spa, yaeL, yfbL, dacA, dacB, dacC, degP/htrA, degQ, iap, mepA, nlpC, pbpG, tsp, ptrA, teas, umuD, ydcP, ydgD, ydhO, yebA, yhbU, yhjJ, and nlpD genes.

In cases where nucleic acid(s) are pre-formed by the parental cell by way of recombinant expression from a prokaryotic expression cassette (either chromosomal or episomal in location) and then packaged inside of the minicells as an immunopotentiator and/or immunotherapeutic, the half-life of the nucleic acid(s) within the minicell is increased by use of minicell-producing bacterial strains harboring one or more deletions or other non-functional mutations in nuclease genes (e.g., the rnc nuclease of *E. coli*) responsible for double stranded RNA degradation. In the absence of the nuclease(s), immunomodulatory nucleic acid molecules and/or immunotherapeutic nucleic acid molecules accumulate to a higher level. This feature is not essential, but is preferred, and can work to increase the potency of immunomodulatory minicells and immunotherapeutic minicells harboring said immunomodulatory and immunotherapeutic nucleic acid molecules.

It is advantageous for minicells intended for use as therapeutic agents in humans to contain few or no viable contaminants, such as viable parental bacterial cells or adventitious microbes introduced during the production process. Most preferably, minicell-based biopharmaceuticals formulated for human use should conform to sterility under U.S. Pharmacopeia <71>. The present disclosure includes by way of reference a method of sterilizing minicell-based biopharmaceutical preparations intended for use in humans by exposure to sterilizing doses of gamma irradiation as described in WO2017/024059, the content of which is hereby expressly incorporated by reference by its entirety.

To further maximize safety and limit toxicity, for example for parenterally administered minicell-based biopharmaceutical products, bacterial minicells (for example, oncolytic bacterial minicells) can be derived from minicell-producing parental bacterial strains containing a deletion of the lpxM/msbB gene. Deletion of the lpxM gene results in the production of de-toxified lipopolysaccharide (LPS) molecules. The lpxM gene (also referred to as the msbB gene) functions to add a terminal myristolic acid group to the lipid A portion of the LPS molecule and removal of this group (by way of elimination of the lpxM gene) results in marked detoxification of LPS by converting LPS from a wild type hex-acylated variety to the less inflammatory penta-acylated variety (lacks the myristolic acid). Specifically, detoxification is characterized by a decrease in the production of pro-inflammatory cytokines in response to exposure to LPS, a process mediated by penta-acylated (mutated) LPS antagonism of Toll-like receptor 4, which leads to a decrease in NF-κB transcriptional activity and global suppression of pro-inflammatory gene expression therewith. It should be noted that this modification does not teach away from the present disclosure as cytokines are still made using the detoxified form of LPS. The detoxification controls only the levels of cytokines produced, making it possible to dampen the acute sepsis-like pro-inflammatory response while allowing for cytokine-mediated immunomodulatory activity levels appropriate for immune efficacy to be achieved without overt toxicity. This deletion can be introduced into any functionally equivalent gene of any Gram-negative minicell-producing strain to achieve the same effect. The enhanced safety profile can reduce the potential for developing sepsis and/or cytokine storm.

From a regulatory and manufacturing perspective, it is also preferred that antibiotic resistance markers be eliminated from the bacterial chromosome of the minicell-producing parental cell strain. The use of most antibiotic resistance gene markers in minicell-producing strains of bacteria is undesirable in order to comply with regulatory requirements imposed by the U.S. Food and Drug Administration (FDA) for use in humans. The FDA will only tolerate the use of the kanamycin resistance gene marker for selection purposes for bacteria or bacterial production strains wherein the final product is intended for use in humans.

Some embodiments provide a method of making minicells, comprising culturing the appropriate minicell-producing bacteria disclosed herein and substantially separating minicells from the minicell-producing parent cells, thereby generating a composition comprising therapeutic minicells or un-modified minicells that may be further processed into therapeutic minicells by addition of additional exogenous components (e.g. small molecule drugs loaded into purified minicells). In some embodiments, minicell formation is initiated on command from an inducible minicell-producing gene by the presence of one or more chemical compounds selected from isopropyl β-D-1-thiogalactopyranoside (IPTG), rhamnose, arabinose, xylose, fructose, melibiose, and tetracycline. In some embodiments, the method further comprises purifying the minicells from the composition. In some embodiments, the minicells are substantially separated from the parent cells by a process selected from the group including but not limited to centrifugation, filtration, ultrafiltration, ultracentrifugation, density gradation, immunoaffinity, immunoprecipitation, and any combination of the preceding purification methods.

The present application describes the novel use of eubacterial minicells and oncolytic eubacterial minicells for purposes of stimulating the immune system in such a way as to have potent and specific anti-tumor effects mediated, in full or in part, by an innate response followed by an adaptive immune response, preferably a tumor-specific CTL response, a process enhanced by exposure of tumor-bearing host to said minicells in vivo. The minicell treatment modalities of the present disclosure can be combined with one or more of immune checkpoint inhibitors, recombinantly expressed tumor specific antigens, patient-specific personalized neo-antigens, CAR-T and CAR-N therapies, radiation therapy, and chemotherapeutic drugs.

Minicell Production

Minicells are achromosomal, membrane-encapsulated biological nanoparticles (approximately 250-500 nm in diameter depending on the strain type and growth conditions used) that are formed by bacteria following a disruption in the normal cell division apparatus. In essence, minicells are small, metabolically active replicas of normal bacterial cells with the exception that they contain no chromosomal DNA and as such, are non-dividing and non-viable. Although minicells do not contain chromosomal DNA, smaller macromolecules such as plasmid DNA, RNA, native and/or recombinantly expressed proteins, and other metabolites have all been shown to segregate into minicells.

Disruptions in the coordination between chromosome replication and cell division lead to minicell formation from the polar region of most rod-shaped prokaryotes. Disruption of the coordination between chromosome replication and cell division can be facilitated through the over-expression of some of the genes involved in septum formation and binary fission. Alternatively, minicells can be produced in strains that harbor mutations in genes involved in septum formation and binary fission. Impaired chromosome segregation mechanisms can also lead to minicell formation as has been shown in many different prokaryotes.

Similarly, minicell production can be achieved by the over-expression or mutation of genes involved in the segregation of nascent chromosomes into daughter cells. For example, mutations in the parC or mukB loci of E. coli have been demonstrated to produce minicells. Both affect separate requisite steps in the chromosome segregation process in Enterobacteriacea. It can be assumed that like the cell division genes described above, manipulation of wild type levels of any given gene involved in the chromosome segregation process that result in minicell production will have similar effects in other family members.

Because the cell division and chromosome replication processes are so critical to survival, there exists a high level of genetic and functional conservation amongst prokaryotic family members with respect to genes responsible for these processes. As a result, the over-expression or mutation of a cell division gene capable of driving minicell production in one family member can be used to produce minicells in another. For example, it has been shown that the over-expression of the E. coli ftsZ gene in other Enterobacteriacea family members such as Salmonella spp. and Shigella spp as well as other class members such as Pseudomonas spp. will result in similar levels of minicell production.

The same can be demonstrated in the mutation-based minicell producing strains of the family Enterobacteriacea. For example, deletion of the min locus in any of Enterobacteriacea family members results in minicell production. Cell division genes from the Enterobacteriacea in which mutation can lead to minicell formation include but are not limited to the min genes (MinCDE). While minicell production from the min mutant strains is possible, these strains have limited commercial value in terms of being production strains. The reason for this is that strains with deletions or mutations within the min genes make minicells at constitutively low levels. This presents two problems in terms of commercialization and economies of scale. The first is that minicell yields from these strains are low, which increases production cost. The second is that minicell yields are highly variable with the mutant strains and lot-to-lot variability has an enormous impact on production cost, manufacturing quality control and regulatory compliance. Using cell division mutant strains to produce minicells that encapsulate biologically active molecules such as proteins, RNA, DNA, and other catabolites for diagnostic or therapeutic delivery is more problematic. This is primarily because the onset of minicell production in the mutant strains cannot be controlled and occurs at a low level so that the end result is that some minicells will contain no biologically active molecules while others will contain widely variable amounts of biologically active molecules. These shortcomings when taken together or separately greatly restrict the utility of these mutant strains for commercial purposes.

Minicell-producing strains that overexpress cell division genes ("over-expressers") are preferred over mutation-based strains because the minicell-production phenotype is controllable if the cell division genes to be overexpressed are placed under the control of an inducible or other conditionally active eubacterial promoter system. Minicell production from strains overexpressing the cell division gene ftsZ were discovered by researchers who were identifying essential cell division genes in E. coli using plasmid-based complementation studies. In these studies, the ftsZ gene was present in over 10 copies per cell. The presence of multiple gene copies of ftsZ was demonstrated to produce minicells and extremely long filamented cells. Ultimately, this transition into the irreversible filamentous phenotype negatively impacts minicell yields from strains overexpressing ftsZ from multi-copy plasmids, although the number of minicells produced is still higher than that of any mutant strain. It has since been demonstrated that by reducing the number of ftsZ gene copies to a single, chromosomal duplication, the number of minicells produced increases over those strains where ftsZ is located on multi-copy plasmids and that the filamentous phenotype is less profound. Thus, the preferred composition(s) are minicell-producing strains that inducibly overexpress the ftsZ gene from a duplicate, chromosomally integrated copy of ftsZ. The duplicate ftsZ gene used can be derived directly from the species of bacteria in which the minicell-production phenotype is being engineered and can also be derived from the ftsZ gene sequence from other species of bacteria. By way of non-limiting example, overexpression of the ftsZ gene of *Escherichia coli* can be used to generate minicells from *Escherichia coli* and *Salmonella typhimurium*. Resulting strains are comprised of the wild type ftsZ gene and a separate, duplicative, and inducible copy of the ftsZ gene on the chromosome and the inducible genetic suicide mechanism(s) described in U.S. patent publication No. 2010/0112670, which is incorporated herein by its entirety. By way of non-limiting example, division genes that can be over-expressed to produce minicells in the family Enterobacteriaceae include but are not limited to ftsZ, minE, sulA, ccdB, and sfiC. The preferred composition is to have a duplicate copy(s) of a cell division gene(s) under the control of an inducible promoter that is stably integrated into the chromosome of a given eubacterial strain. It is easily recognized by one skilled in the art that this same strategy could be imparted if the inducible cell division gene cassette were present on a plasmid, cosmid, bacterial artificial chromosome (BAC), recombinant bacteriophage or other episomal DNA molecule present in the cell.

This inducible phenotype approach to minicell production has several distinct advantages over the mutant systems. The first is that because there are no constitutive genetic mutations in these strains, there exists no selective pressure during normal growth and the cells of the culture maintain a very stable and normal physiology until the minicell phenotype is induced. The result is that inducible minicell producing strains are healthier and more stable, which ultimately results in higher yields of minicells. Another distinct advantage of using the inducible phenotype approach to minicell production is in cases where minicells are to be used to deliver biologically active molecules such as proteins, therapeutic RNAs, plasmid DNAs, and other bioactive catabolites that can be made by the minicell-producing parent cells such that the minicells that are produced encapsulate those biologically active molecules. In these cases, the preferred method is to induce the formation of the biologically active molecule(s) within the parental cells prior to inducing the minicell phenotype, so that all of the minicells produced will contain the desired amount of the biologically active molecule(s). Alternatively, the minicells themselves can produce the bioactive molecule after being separated from the parental cells. This includes but is not limited to forming the bioactive molecule from an episomal nucleic acid or RNA encoding for the bioactive molecule located within the minicell or by preexisting protein constituents of minicells after being separated from the parental cells. Any of these expression strategies can be employed to express and display binding moieties on the surfaces of minicells. These advantages, when used in combination, result in a higher quality and quantity of minicells. In addition, these minicells can further comprise small molecule drugs that can be loaded into minicells as described in more detail below.

Minicell Purification, Formulation, and Sterilization

Because minicells are derived from some bacteria that are pathogenic or opportunistically pathogenic, it is of the utmost importance that any viable contaminating parental cells be functionally eliminated from a given population before administration. Conventionally, live parental cells have been eliminated through either physical means or biological means or both.

Physical means include the use of centrifugation-based separation procedures, filtration methodologies, chromatography methodologies, or any combination thereof.

Biological elimination is achieved by but not limited to the preferential lysis of parental cells, the use of auxotrophic parental strains, treatment with antibiotics, treatment with non-ionizing UV radiation, diaminopimelic acid (DAP) deprivation, selective adsorption of parental cells, treatment with other DNA damaging agents, and induction of a suicide gene.

Preferential lysis of parental cells is typically mediated by inducing the lytic cycle of a lysogenic prophage. In the case of minicell producing strains, it is most useful to use a prophage that is lysis competent but defective at re-infection, such that minicells are not subsequently infected and lysed during activation of the lytic phenotype. Alternatively, and by way of non-limiting example, individual genes such as those classified as members of the holin gene family, can be expressed to achieve similar levels of lysis without the concerns over re-infection inherent to the use of lysogenic prophages. Both approaches are limited by the fact that the lysis event, regardless of the method used to achieve it, expels unacceptable amounts of free endotoxin into the media. Removal of such large amounts of free endotoxin is time consuming, suffers from lot to lot variability, and is ultimately cost prohibitive.

The use of auxotrophic strains raises concerns over reversion and as such can only be used in cases where minicells are to be produced from commensal or non-pathogenic strains of bacteria. Thus, their application is limited with respect to being used as a method for elimination of live non-pathogenic parental cells used in minicell production.

Treatment with non-ionizing UV irradiation can be useful in the elimination of live parental cells on a minicell production run except for the fact that UV irradiation is random with respect to its effects on nucleic acids and results are highly variable from lot to lot. In addition, this method is not preferred when using minicells to deliver therapeutic or prophylactic nucleic acids as UV irradiation randomly damages all nucleic acids. For instance, plasmid DNA would also be highly susceptible to DNA damage by UV irradiation and may be rendered ineffective although still effectively delivered by minicells.

Diaminopimelic acid (DAP) deprivation can be useful in the elimination of live parental cells with the exception that this approach is limited by the number of species it can be used for. In other words, not all parent cell species capable of producing minicells require DAP for survival. DAP mutants in *E. coli* minicell-producing strains are of great advantage and in some cases preferred over the wild type. The advantage of using DAP is that this compound (di-aminopimelic acid, an *E. coli* cell wall constituent) is critical for the growth of *E. coli* and is not present in or produced by animals. Thus, should a "viable" *E. coli* minicell-producing parental cell be administered along with targeted minicells, the parental cell will be unable to grow and will thereby be inert to the animal and with respect to minicell activity. A similar approach can be used with *Salmonella* spp. based minicell-producing parental strains except in that case the aro genes, preferably aroB are removed.

Selective adsorption methodologies have yet to be explored with respect to purifying minicells from viable parental cells. Selective adsorption is defined as any process by which parental cells or minicells are preferentially adsorbed to a substrate by their affinity for the substrate. By way of non-limiting example, high affinity protein-protein interactions could be exploited for this use. By way of non-limiting example, the novel minicell outer membrane protein Lpp-OmpA::Protein A has a high affinity for the Fc region of most antibodies. The gene encoding for Lpp-OmpA::Protein A is under the control an inducible promoter could easily be introduced on to the chromosome of an immunomodulatory minicell producing strain. Immunomodulatory minicells could be produced from this strain prior to the activation of expression of the invasin gene such that the minicells produced do not express or display Lpp-OmpA::Protein A on their cell surface. Once the desired quantity of immunomodulatory minicells is produced from the strain, the viable cells within the culture could be given the signal to produce the Lpp-OmpA::Protein A protein such that Lpp-OmpA::Protein A is only expressed and displayed upon viable cells. Once Lpp-OmpA::Protein A is preferentially expressed on the surface of viable parental cells, they can be easily adsorbed to a substrate coated with antibodies or other Fc-region containing proteins. Once absorbed, minicells can be selectively purified away from viable parental cells by a number of different means dependent upon the substrate type used. Substrates include but are not limited to solid-phase chromatographic columns used in gravity filtration applications, magnetic beads, ion exchange columns, or HPLC columns.

In some embodiments, minicells are substantially separated from the minicell-producing parent cells in a composition comprising minicells. For example, after separation, the composition comprising the minicells is more than about 99.9%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35% or 30% free of minicell-producing parent cells. In some embodiments, the composition contains less than about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% minicell-producing parent cells.

Most preferably, minicell-based biopharmaceuticals formulated for human use, especially parenteral use, should be terminally sterilized by exposure to ionizing gamma irradiation and conform to sterility under U.S. Pharmacopeia <71>. The present disclosure includes, by way of reference, a method of sterilizing minicell preparations intended for use in humans by exposure to sterilizing doses of ionizing gamma irradiation. Such referenced methods are described in PCT/US2016/045400 and incorporated herein. Some embodiments disclosed herein provide a method of making bacterial minicells, comprising culturing minicell-producing bacteria to produce minicells and substantially separating minicells from the minicell-producing parent cells, thereby generating a composition comprising minicells. In some embodiments, the method further comprises inducing minicell formation from a culture of minicell-producing parent cells. In some embodiments, minicell formation is induced by the presence of one or more chemical compounds selected from isopropyl E-D-1-thiogalactopyranoside (IPTG), rhamnose, arabinose, xylose, fructose, melibiose, and tetracycline. In some embodiments, the method further comprises purifying the minicells from the composition. In some embodiments, the minicells are substantially separated from the parent cells by a process selected from the group including but not limited to centrifugation, filtration, ultrafiltration, ultracentrifugation, density gradient(s), immunoaffinity, immunoprecipitation, and any combination of the preceding purification methods. In some embodiments, minicells are lyophilized. In some embodiments, minicells are frozen. In some embodiments, minicells are lyophilized and then frozen. In some embodiments, minicells are formulated as a frozen suspension in a cryoprotectant excipient or other pharmaceutically acceptable carrier or GRAS substance. In some embodiments, minicells are exposed to ionizing irradiation. In some embodiments, minicells are terminally sterilized by exposure to ionizing irradiation. In some embodiments, minicells are terminally sterilized by exposure to ionizing gamma irradiation. A non-limiting example of excipient in the formulation of minicells to be subjected to terminal sterilization by ionizing irradiation is D-trehalose in sterile water. Alternative concentrations of D-trehalose or alternative diluents may be used, and one of the preferred concentrations of D-trehalose is 12% (w/v) and one of the preferred diluents is sterile water.

Disclosed herein include methods and compositions for terminal sterilization of bacterial minicell compositions, for example by ionizing irradiation. Once therapeutic, immunomodulatory, and/or immunogenic minicells are generated, formulated, filled into pharmaceutically acceptable containers, including but not limited to vials or syringes, they are sealed and subjected to terminal sterilization with ionizing irradiation in said container. Non-limiting examples of ionizing irradiation include gamma irradiation, high frequency electromagnetic irradiation, E-beam (electron beam, beta irradiation) irradiation, X-ray (photon) irradiation, and UV irradiation. One of the preferred type of ionizing irradiation for use in the methods and compositions disclosed herein is gamma irradiation.

The dose of ionizing irradiation suitable for use in the methods and compositions disclosed herein can vary. In some embodiments, the dose of ionizing irradiation required for reducing parental cell and adventitious microbial bioburden(s) to acceptable standards of sterility can be empirically determined. Non-limiting exemplary range of the irradiation dose is between 5 kGy and 40 kGy, for example the irradiation can be at a dose of, or at a dose of about, 5 kGy, 8 kGy, 10 kGy, 11 kGy, 12 kGy, 13 kGy, 14 kGy, 15 kGy, 16 kGy, 17 kGy, 18 kGy, 19 kGy, 20 kGy, 21 kGy, 22 kGy, 23 kGy, 24 kGy, 25 kGy, 28 kGy, 30 kGy, 35 kGy, 40 kGy, or a range between any of these values. In some embodiments, the irradiation is at a dose of about 5 kGy to about 30 kGy, or about 10 kGy to about 25 kGy. In some embodiments, the irradiation is at a dose of 25 kGy. The composition comprising minicells suitable for being irradiated for sterilization can be in various forms, including and not limited to, liquid suspension, frozen suspension, and freeze-dried lyophilized (lyophile) cake formulations. In some embodiments, the formulation for sterilization by ionizing irradiation for the composition comprising minicells is a frozen suspension or frozen lyophile. In some embodiments, terminal sterilization of the composition comprising minicells by ionizing irradiation comprises, or is, terminally sterilizing ionizing gamma irradiation at a dose of 25 kGy.

Sterility of a minicell-based biopharmaceutical product can be determined using methods known in the art, for example, as described in USP <71> standards under version USP 38 NF 33. In summary, sterility under USP <71> is defined as no growth (turbidity compared to negative control) in Fluid Thioglycollate Medium (medium sterilized by a validated process) incubated at 32.5° C.±2.5° C. over a 14-day span, post irradiation. Per USP <71>, if the minicell biopharmaceutical product is formulated in liquid of 1 mL or less, and entire vial is used to inoculate growth medium for sterility testing. If over 1 mL but less than 40 mL, half the container but no less than 1 mL is to be used to inoculate sterility test medium. If greater than 40 mL but less than 100 mL, 20 mL shall be used. If over 100 mL, 10% of the container contents, but not less than 20 mL is to be used. If formulated as a solid, including a lyophile, then if less than 50 mg, the entire container contents must be used. If greater than 50 mg and less than 300 mg, then half the mass, but not less than 50 mg is to be used. If greater than 300 mg and less than 5 g, 150 mg is to be used. If greater than 5 g, 500 mg is to be used. The number of containers to be tested in a given production lot under USP <71> include, if less than 100 containers, 10% or 4 containers, whichever is greatest. If greater than 100 containers but fewer than 500, 10 containers are to be used. If more than 500 containers, 2% or 20 containers, whichever is less. For ophthalmic and other non-injectable biopharmaceutical products, if not more than 200 containers, 5% or 2 containers, whichever is greater. If more than 200 containers, 10 containers are to be tested.

Targeting Minicells to Specific Cells, Tissues, and Organs

There are two general approaches to making minicells targeting competent (i.e., able to target select cell, tissue, or organ types, particularly tumor cells, tumor endothelial cells, or other tumor stromal cells). The first approach is to express and display on the minicell-surface, different surface localized bacterial proteins including, but not limited to, invasins, adhesins, intimins, pili, and flagella.

For example, recombinant expression of invasin from *Yersinia pseudotuberculosis* on the surface of minicells results in "integrin-targeted minicells". Invasin is highly selective for mammalian alpha3beta1 and alpha5beta1 integrins that are in the "active" and "unligated" conformation. These integrin conformational subtypes are involved in cell migration and adhesion and therefore found primarily in the context of cancer, cancer metastasis, angiogenesis, and are not normally found in this conformation in normal tissues. Integrin-targeted oncolytic minicells are used as targeted delivery vehicles to target specific cell types that have elevated expression and/or activity of beta1-integrins and are involved in disease in vivo. The targeted integrin-targeted minicells disclosed herein are targeted to eukaryotic cancer cell-specific surface antigens that include but are not limited to integrin $\alpha3\beta1$, integrin $\alpha4\beta1$, integrin $\alpha5\beta1$, integrin $\alpha6\beta1$, integrin $\alpha_{v\beta1}$, and integrin $\beta1$.

The second targeting approach is antibody-based. Antibody-based targeting of minicells and oncolytic minicells to tumor or other cells is mediated by the surface display of antibodies or common antibody derivatives, such as single chain antibodies. Several methodologies for functionalizing the surface of minicells with targeting antibodies have been described. In one approach, antibodies and antibody derivatives are physically attached to the surface of minicells to make them targeting-competent. Physical attachment methods include chemical cross-linking, the use of bi-specific antibodies and antibody derivatives, and the attachment of Fc-containing antibodies and antibody derivatives to minicells containing the Fc-binding portion of Protein A or Protein G on their surfaces. As an alternative to the physical attachment of antibodies to minicells, a host of different recombinant membrane anchored fusion proteins capable of displaying functional single chain antibody fragments on the minicells surface can be employed. Methods for making minicells targeting competent by addition of antibodies to their surfaces are incorporated by reference to U.S. Pat. No. 7,183,105 and U.S. patent application Ser. No. 13/397,313 published as US2012/0207754, the content of which is hereby incorporated by reference.

Loading Payloads into Minicells

Eubacterial minicells are capable of encapsulating and delivering several classes of biologically active compounds that have therapeutic, prophylactic, or diagnostic benefit to an animal. Types of the biologically active compounds (payloads) that can be delivered by minicells include but are not limited to small molecules (including small molecule drugs), nucleic acids, polypeptides, radioisotope, lipids, lipopolysaccharides, and any combination thereof.

Proteins are comprised of polypeptides and are encoded by DNA. Proteins can be biologically functional, such as enzymes, toxins, or signaling proteins. Proteins can be structural, such as is the case for actin and the like. Proteins can bind tightly to other proteins, such as with antibodies and antibody mimetics, and be used to disrupt functions requiring protein/protein interactions. Proteins can provide detection signals by being fluorescent or bioluminescent. Proteins can serve as immunogens or serve other therapeutic purposes (such as supplying or restoring an enzyme in a target cell, tissue, organ, or animal). Proteins can aid in the post-endocytosis intracellular transfer of other payload types. For example, proteins such as listeriolysin O from *Listeria monocytogenes* can be employed to facilitate the transfer of other minicell payload(s) from the endocytic compartment(s) of a target cell into the cytosol of a target cell. Proteins can also be pro-drug converting enzymes. Recombinantly expressed/produced therapeutic, immunomodulatory, and immunotherapeutic polypeptides to be delivered by targeted minicells include, but are not limited to, protein toxins, cholesterol-dependent cytolysins, functional enzymes, antibody mimetics, protein/protein interaction disrupters, activated caspases, pro-caspases, cytokines, chemokines, receptor traps, including chemokine receptor traps and cytokine receptor traps, cell-penetrating peptides, and any combination of the proceeding. Recombinant expression of a therapeutic polypeptide(s) can be the result of expression from any of the various episomal recombinant prokaryotic expression vectors known in the art including but not limited to plasmids, cosmids, phagemids, and bacterial artificial chromosomes (BACs), and any combination of the preceding. In similar fashion, recombinant expression can be achieved by a chromosomally located prokaryotic expression cassette present in one or more copies of the minicell-producing parent cell chromosome. The delivery of protein toxins using the targeted minicells disclosed herein is a particularly attractive approach in applications where selective elimination of cells in vivo is desirable. Examples of protein toxins include, but are not limited to, gelonin, diphtheria toxin fragment A, diphtheria toxin fragment A/B, tetanus toxin, *E. coli* heat labile toxin (LTI and/or LTII), cholera toxin, *C. perfringes* iota toxin, *Pseudomonas* exotoxin A, shiga toxin, anthrax toxin, MTX (*B. sphaericus* mosquilicidal toxin), streptolysin, barley toxin, mellitin, anthrax toxins LF and EF, adenylate cyclase toxin, botulinolysin B, botulinolysin E3, botulinolysin C, botulinum toxin A, cholera toxin, *clostridium* toxins A, B, and alpha, ricin, shiga A toxin, shiga-like A toxin, cholera A toxin, pertussis Si toxin, and *E. coli* heat labile toxin (LTB). Polypeptides that confer oncolytic properties to minicells include, but are not limited to, perfringolysin O (PFO), pH stable variants of listeriolysin O (pH-independent; amino acid substitution L461T), thermostable variants of listeriolysin O (amino acid substitutions E247M, D320K), pH and thermostable variants of listeriolysin O (amino acid substitutions E247M, D320K, and L461T), streptolysin O, streptolysin O c, streptolysin O e, sphaericolysin, anthrolysin O, cereolysin, thuringiensilysin O, weihenstephanensilysin, alveolysin, brevilysin, butyriculysin, tetanolysin O, novyilysin, lectinolysin, pneumolysin, mitilysin, pseudopneumolysin, suilysin, intermedilysin, ivanolysin, seeligeriolysin O, vaginolysin, and pyolysin. Protein toxins can be localized to different sub-cellular compartments of the minicell at the discretion of the artisan. When targeted minicells disclosed herein are derived from a Gram-negative parental minicell-producing strain, recombinantly expressed therapeutic polypeptides produced therefrom can be localized to the cytosol, the inner leaflet of the inner membrane, the outer leaflet of the inner membrane, the periplasm, the inner leaflet of the outer membrane, the outer membrane of minicells, and any combination of the proceeding. When targeted minicells disclosed herein are derived from a Gram-positive parental minicell-producing strain, recombinantly expressed therapeutic polypeptides produced therefrom can be localized to the cytosol, the cell wall, the inner leaflet of the membrane, the membrane of minicells, and any combination of the proceeding. In some embodiments, the bacterial minicells do not comprise any exogenous protein toxin other than PFO. In some embodiments, the bacterial minicells do not comprise any exogenous therapeutic compounds (e.g., therapeutic proteins) other than PFO.

All classes of nucleic acids, including, but not limited to, synthetic nucleic acid subtypes, may be delivered by minicells. Minicells delivering nucleic acids are designed to exert a therapeutic effect, including but not limited to an immunotherapeutic effect that can stem from gene transfer, gene silencing, Toll-like receptor antagonism/agonism, and other nucleic acid-based mechanisms known in the art. Double-stranded plasmid DNA molecules segregate naturally into minicells during minicell production and are easily engineered to contain eukaryotic expression sequences capable of being expressed by the recipient eukaryotic cell/host organism. Any sequence can be coded into an expression plasmid and preferred sequences include those for protein toxins, cytokines, chemokines, vaccine antigens, including but not limited to, cancer vaccine antigens and personalized neo-antigens, short hairpin RNA sequences, siRNA sequences, micro-RNA sequences, and the like. In a separate approach, small nucleic acids, including but not limited to, those ranging from 2-1,000 base pairs in length, may be loaded into purified minicells by passive diffusion (i.e. co-incubation with minicells and nucleic acid mixture). Although unnecessary for utility of this application, the passive diffusion process of nucleic acids into minicells may be enhanced by standard electroporation techniques known in the art.

Small molecules, including but not limited to, small molecule drugs such as chemotherapeutic agents, are also loaded into purified minicells by passive diffusion facilitated by co-incubation of the small molecule drug with purified minicells. Because minicells are metabolically inactive or have limited and finite metabolic capacity, efflux pumps of minicells are essentially inactive, leading to retention of small molecule drugs. Preferred small molecule drugs include, but are not limited to, chemotherapeutic agents and anti-metabolites. Minicells delivering small molecule drugs targeting the IDO1 and ARG-1 pathways enhance immune activation by lifting the immunosuppressive effects of their respective end-product catabolites. For example, minicells delivering an IDO1 inhibitor, such as epacadostat, directly to myeloid derived suppressor cells or tumor-associated macrophages synergizes with the IDO1 inhibitor by blocking indoleamine 2,3-dioxygenase activity while the minicell component provides immunostimulatory activity. This approach is then further combined with immune checkpoint blockade therapy.

Immune Checkpoint Inhibitors

The immune system plays an important role in the prevention of cancer. It is becoming increasingly clear that T-cell and Natural Killer (NK) cell mediated cytolytic responses directed towards to tumors are an attractive therapeutic approach in the treatment of cancer. In addition, it has also become clear that many tumors express immunosuppressive molecules and secrete factors that recruit and maintain immunosuppressive cells as a mechanism of immune evasion. These immunosuppressive molecules are collectively referred to as "immune checkpoints" and many antibody-based immune checkpoint inhibitor therapies are gaining market approval and/or are in various stages of clinical and preclinical development. In general, the goal of immune checkpoint inhibitor therapy is to reverse the immunosuppressive signaling events responsible for suppressing T-cell function in the tumor microenvironment, thereby restoring T-cell activity against the tumor. Immune suppression at the level of immune checkpoints is facilitated by either an enhanced inhibitory response or curtailed co-stimulatory T-cell signaling. As such, there are two emerging classes of immune checkpoint inhibitor therapies; namely, those immune checkpoint therapies directed at enhancing co-stimulatory signaling, or those directed at blocking inhibitory signaling pathways. At present, clinical effectiveness of these inhibitors are thought to be tied in part to mutational load of individual tumors (i.e. the total number of mutations in a given tumor type), as this results in an increase in the repertoire of tumor-selective neoantigens produced by a given tumor. In addition, many tumors have adapted phenotypes that do not support proper degradation of proteins, display of antigens, or expression of MHC-I (to present neo-antigen peptides). Tumors with this phenotype(s) are particularly difficult to manage with immune checkpoint inhibitor therapies for the simple reason that T-cells reactivated through checkpoint blockade are only effective against those tumors that sufficiently and properly display antigens through MHC-I.

The innate immune system contributes greatly to global immunosuppressive effects as many tumors secrete factors that stimulate and perpetuate aberrant myelopoiesis. Aberrant myelopoiesis stimulates the production, release, and recruitment of immature myeloid-derived suppressor cells (MDSCs) to the tumor microenvironment where they propagate and maintain an immunosuppressive environment. It is widely accepted that MDSCs differentiate into tumor-associated macrophages (TAMs), which then provide consistent tumor resident immunosuppressive signals that help to upregulate immune checkpoint molecules, prevent T-cell activation, promote T-cell exhaustion, and support immunosuppressive regulatory T-cell survival and activity. MDSCs and TAMs also contribute to immunosuppression at the metabolic level by expressing high levels of IDO1 and ARG1. These two metabolic enzymes produce catabolites from tryptophan and arginine that have local immunosuppressive effects.

There is a need for additional therapies that can help to overcome peripheral tolerance within tumors by reversing immunosuppression, exposing immune cells to tumor antigens, and ultimately re-programming the tumor immune environment to help restore adaptive immune surveillance against tumors. These therapies can work on their own to achieve the desired results, but can also be combined with immune checkpoint inhibitors to synergistically restore immune activity against tumors. Some treatment modalities have been demonstrated to expose tumor antigens and aid in immune recognition of tumors. However, each has its own unique limitation(s). For example, some commonly used chemotherapy drugs have been suggested to prime the immune system by driving tumor cell apoptosis and promoting cross-presentation of tumor antigens in the process. The problem with this approach is that the same chemotherapeutic drugs often simultaneously cripple the immune system and its ability to react to exposed tumor antigens. Two other relevant non-chemotherapeutic drug examples include radiation therapy and the use of oncolytic viruses. Radiation therapy can suffer from the same limitations as chemotherapeutic drugs as it non-specifically destroys both tumor cells and surrounding healthy tissues, including immune cells of the tumor microenvironment. Treatment with radiation would therefore require the recruitment, trafficking, and activation of new T-cells to the tumor microenvironment to stimulate anti-tumor cellular responses primed by neoantigen exposure. It is not clear that the timing of recruitment and trafficking of new T-cells to the tumor microenvironment following radiation sufficiently overlaps with neoantigen exposure. Oncolytic viruses overcome this challenge by not significantly disturbing immune cells of the tumor microenvironment, but introduce new challenges and limitations of their own. Challenges include toxicity owing to off-target effects and/or somatic chromosomal integration, pre-existing immunity to viral vectors that impart a negative effect on pharmacokinetics and exposure, and inconsistent expression of virally encoded transgenes. Limitations of oncolytic viruses include small coding capacities, reliance upon tumor selective promoters, limited opportunities for systemic administration due to preferential accumulation in the liver, and lack of any inherent immunostimulatory adjuvant properties. To overcome the latter limitation, new age oncolytic viruses have been engineered to express immune activators such as GM-CSF or interferons. However, this approach would not be expected to result in comprehensive immune activation at the tumor site as it takes multiple different cytokines and other immune effector molecules beyond GM-CSF and interferons to stimulate and sustain immune responses. Single cytokine or chemokines do not invoke the full spectrum of Th1 immune responses needed to have a robust anticancer effect as these factors work in concert at varying levels that are dynamic over time.

There is a need to develop therapies that aid in the exposure of neo-antigens, immune stimulation, reversal of immunosuppression, and immune protection against tumors. Disclosed herein are novel uses of bacterial minicells, for example oncolytic bacterial minicells, to stimulate tumor-specific immunity. As disclosed herein, the bacterial minicells can be used alone, or in combination with one or more immune checkpoint inhibitors, to, for example, stimulate tumor specificity immunity.

Immune checkpoint inhibitors are compounds that prevent immune cells from being turned off by cancer cells. Immune checkpoint inhibitors have been used as cancer treatment drugs. Examples of immune checkpoint inhibitors include, but are not limited to, inhibitors of CTLA4 (cytotoxic T lymphocyte antigen-4), PD-1 (programmed cell death protein 1), PD-L1 (programmed cell death ligand 1), PD-L2 (programmed cell death ligand 2), PD-L3 (programmed cell death ligand 3), PD-L4 (programmed cell death ligand 4), LAG-3 (lymphocyte activation gene-3), TIM-3 (T cell immunoglobulin and mucin protein-3), B7-H3, B7-H4, Indoleamine-pyrrole 2,3-dioxygenase (IDO), glucocorticoid-induced TNFR-related protein (GITR), 4-1BB (CD137), OX40 (CD-134), CD27, KIR2DL, CSF1R, CD40L, and KIR (killer immunoglobulin receptor). In some embodiments, the immune checkpoint inhibitor is a binding ligand of PD-1. In some embodiments, the immune checkpoint inhibitor is a binding ligand of CTLA-4. In some embodiments, the immune checkpoint inhibitor is an antibody (e.g., a monoclonal antibody) that targets PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, KIR, or a combination thereof.

In some embodiments, the immune checkpoint inhibitor is a small peptide that can inhibit T cell regulation function. In some embodiments, the immune checkpoint inhibitor is a small molecule (e.g. less than 500 Daltons) that can inhibit T cell regulation function. In some embodiments, the immune checkpoint inhibitor is a molecule providing co-stimulation of T-cell activation. In some embodiments, the immune checkpoint inhibitor is a molecule providing co-stimulation of natural killer cell activation. In some embodiments, the immune checkpoint inhibitor is an antibody. The antibody can be, for example, α-CD3-APC, α-CD3-APC-H7, α-CD4-ECD, α-CD4-PB, α-CD8-PE-Cy7, α-CD-8-PerCP-Cy5.5, α-CD11c-APC, α-CD11b-PE-Cy7, α-CD11b-AF700, α-CD14-FITC, α-CD16-PB, α-CD19-AF780, α-CD19-AF700, α-CD20-PO, α-CD25-PE-Cy7, α-CD40-APC, α-CD45-Biotin, Streptavidin-BV605, α-CD62L-ECD, α-CD69-APC-Cy7, α-CD80-FITC, α-CD83-Biotin, Streptavidin-PE-Cy7, α-CD86-PE-Cy7, α-CD86-PE, α-CD123-PE, α-CD154-PE, α-CD161-PE, α-CTLA4-PE-Cy7, α-FoxP3-AF488 (clone 259D), IgG1-isotype-AF488, α-ICOS (CD278)-PE, α-HLA-A2-PE, α-HLA-DR-PB, α-HLA-DR-PerCPCy5.5, α-PD1-APC, VISTA, co-stimulatory molecule OX40, and CD137.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. The term "PD-1" as used herein includes human PD-1 (hPD-1), variants, isoforms, and species homologs of hPD-1, and analogs having at least one common epitope with hPD-1. Various cell surface glycoprotein ligands for PD-1 have been identified, including PD-L1, PD-L2, PD-L3, and PD-L4, that are expressed on antigen-presenting cells as well as many human cancers and have been shown to downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The term "PD-L2" as used herein includes human PD-L2 (hPD-L2), variants, isoforms, and species homologs of hPD-L2, and analogs having at least one common epitope with hPD-L2. The term "PD-L3" as used herein includes human PD-L3 (hPD-L3), variants, isoforms, and species homologs of hPD-L3, and analogs having at least one common epitope with hPD-L3. The term "PD-L4" as used herein includes human PD-L4 (hPD-L4), variants, isoforms, and species homologs of hPD-L4, and analogs having at least one common epitope with hPD-L4. In some embodiments, the immune checkpoint inhibitor is Pembrolizumab (Keytruda) or Nivolumab (Opdivo). In some embodiments, the immune checkpoint inhibitor is Atezolizumab (Tecentriq). In some embodiments, the immune checkpoint inhibitor is Ipilimumab (Yervoy). In some embodiments, the immune checkpoint inhibitor is nivolumab, pembrolizumab, pidilizumab, ipilimumab, dacarbazine, BMS 936559, durvalimumab, avelumab, or any combinations thereof.

CTLA-4 is a protein receptor that, functioning as an immune checkpoint, downregulates the immune system. CTLA4 is a member of the immunoglobulin (Ig) superfamily found on the surface of T cells. CTLA-4 comprises a single extracellular Ig domain. CTLA-4 transcripts have been found in T cell populations having cytotoxic activity, suggesting that CTLA-4 might function in the cytolytic response.

In some embodiments, minicells, including, but not limited to, oncolytic minicells, are capable of reversing immunosuppression at the innate level by one or mechanism(s). Such mechanisms include: (i) selective elimination of immunosuppressive myeloid derived suppressor cells, (ii) re-polarization and/or differentiation of immunosuppressive myeloid derived suppressor cells, (iii) re-polarization and/or differentiation of tumor-associated macrophages, (iv) promoting maturation and activation of plasmacytoid dendritic cells away from a tolerogenic phenotype, and (v) any combination of the preceding. Minicells, for example, oncolytic minicells, that exert this mechanism of action do so within the isolated peripheral tumor microenvironment, at metastatic sites, and in the peripheral blood and lymphoid tissues of cancer patients following administration. Combined treatment with minicells, particularly oncolytic minicells, with therapies that target innate immune cells and pathways are used to synergistically overcome innate immunosuppression. Such innate targeted therapies include, but are not limited to, IDO1 inhibitors, ARG1 inhibitors, prostaglandin inhibitors, antibody therapies directed at chemokines such as CSF-1, antibodies or small molecules or other agents targeting innate chemokine receptors (e.g. CSF1R), and the like.

Administration and Pharmaceutical Compositions

The present application also relates to compositions, including but not limited to pharmaceutical compositions comprising any of the bacterial minicells and/or one disclosed herein or more immune checkpoint inhibitors. In some embodiments, the composition (e.g., the pharmaceutical composition) comprises the bacterial minicells but not immune checkpoint inhibitors. For example, provided herein include, in some embodiments, a first composition comprising the bacterial minicells and a second composition comprising one or more immune checkpoint inhibitors. In some embodiments, the composition (e.g., the pharmaceutical composition) comprises the bacterial minicells and one or more immune checkpoint inhibitors. The immune checkpoint inhibitors can be, for example, inhibitors of PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, and KIR. The term "composition" used herein refers to a mixture comprising at least one carrier, preferably a physiologically acceptable carrier, and one or more minicell compositions. The term "carrier" used herein refers to a chemical compound that does not inhibit or prevent the incorporation of the biologically active peptide(s) into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution; an ointment; a paste, an aerosol, a droplet, a colloid or an emulsion etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the minicell composition is disposed.

A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" used herein includes any medium or material that is not biologically or otherwise undesirable, i.e., the carrier can be administered to an organism along with a minicell composition without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application. The terms "therapeutically effective amount" and "pharmaceutically effective amount" refer to an amount sufficient to induce or effectuate a measurable response in the target cell, tissue, or body of an organism. What constitutes a therapeutically effective amount will depend on a variety of factors, which the knowledgeable practitioner will consider in arriving at the desired dosage regimen.

The compositions can also comprise other chemical components, such as diluents and excipients. A "diluent" is a chemical compound diluted in a solvent, preferably an aqueous solvent, that facilitates dissolution of the composition in the solvent, and it can also serve to stabilize the biologically active form of the composition or one or more of its components. Salts dissolved in buffered solutions are utilized as diluents in the art. For example, preferred diluents are buffered solutions containing one or more different salts. An unlimiting example of preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a given compound or pharmaceutical composition.

An "excipient" is any inert substance that can be added to a composition to confer a suitable property, for example, a suitable consistency or to produce a drug formulation. Suitable excipients and carriers include fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropyl-methyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan. Chitosan microspheres and microcapsules can be used as carriers. See e.g., WO 98/52547 (which describes microsphere formulations for targeting compounds to the stomach, the formulations comprising an inner core (optionally including a gelled hydrocolloid) containing one or more active ingredients, a membrane comprised of a water insoluble polymer (e.g., ethylcellulose) to control the release rate of the active ingredient(s), and an outer layer comprised of a bioadhesive cationic polymer, for example, a cationic polysaccharide, a cationic protein, and/or a synthetic cationic polymer; U.S. Pat. No. 4,895,724. Typically, chitosan is cross-linked using a suitable agent, for example, glutaraldehyde, glyoxal, epichlorohydrin, and succinaldehyde. Compositions employing chitosan as a carrier can be formulated into a variety of dosage forms, including pills, tablets, microparticles, and microspheres, including those providing for controlled release of the active ingredient(s). Other suitable bioadhesive cationic polymers include acidic gelatin, polygalactosamine, polyamino acids such as polylysine, polyhistidine, polyornithine, polyquaternary compounds, prolamine, polyimine, diethylaminoethyldextran (DEAE), DEAE-imine, DEAE-methacrylate, DEAE-acrylamide, DEAE-dextran, DEAE-cellulose, poly-p-aminostyrene, polyoxethane, copolymethacrylates, polyamidoamines, cationic starches, polyvinylpyridine, and polythiodiethylaminomethylethylene.

The compositions can be formulated in any suitable manner. Minicell compositions may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition disclosed herein is compressed into tablet or pill form suitable for oral administration or compounded into a sustained release formulation. When the composition is intended for oral administration to be delivered to epithelium in the intestines, it is preferred that the formulation be encapsulated with an enteric coating to protect the formulation and prevent premature release of the minicell compositions included therein. As those in the art will appreciate, the compositions disclosed herein can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Some preferred embodiments provide compositions that comprise a bioadhesive, preferably a mucoadhesive, coating. A "bioadhesive coating" is a coating that allows a substance (e.g., a minicell composition) to adhere to a biological surface or substance better than occurs absent the coating. A "mucoadhesive coating" is a preferred bioadhesive coating that allows a substance, for example, a composition to adhere better to mucosa occurs absent the coating. For example, minicells can be coated with a mucoadhesive. The coated particles can then be assembled into a dosage form suitable for delivery to an organism. Preferably, and depending upon the location where the cell surface transport moiety to be targeted is expressed, the dosage form is then coated with another coating to protect the formulation until it reaches the desired location, where the mucoadhesive enables the formulation to be retained while the composition interacts with the target cell surface transport moiety.

Compositions disclosed herein can be administered to any organism, preferably an animal, preferably a mammal, bird, fish, insect, or arachnid. Preferred mammals include bovine, canine, equine, feline, ovine, and porcine animals, and non-human primates. Humans are particularly preferred. Multiple techniques of administering or delivering a compound exist in the art including, but not limited to, oral, rectal (e.g. an enema or suppository) aerosol (e.g., for nasal or pulmonary delivery), parenteral, and topical administration. Preferably, sufficient quantities of the biologically active peptide are delivered to achieve the intended effect. The particular amount of composition to be delivered will depend on many factors, including the effect to be achieved, the type of organism to which the composition is delivered, delivery route, dosage regimen, and the age, health, and sex of the organism. As such, the particular dosage of a composition incorporated into a given formulation is left to the ordinarily skilled artisan's discretion.

Those skilled in the art will appreciate that when the compositions disclosed herein are administered as agents to achieve a particular desired biological result, which can include a therapeutic, diagnostic, or protective effect(s) (including vaccination), it may be possible to combine the minicell composition with a suitable pharmaceutical carrier. The choice of pharmaceutical carrier and the preparation of the minicells as a therapeutic or protective agent will depend on the intended use and mode of administration. Suitable formulations and methods of administration of therapeutic agents include those for oral, pulmonary, nasal, buccal, ocular, dermal, rectal, intravenous, or vaginal delivery.

Depending on the mode of delivery employed, the context-dependent functional entity can be delivered in a variety of pharmaceutically acceptable forms. For example, the context-dependent functional entity can be delivered in the form of a solid, solution, emulsion, dispersion, and the like, incorporated into a pill, capsule, tablet, suppository, aerosol, droplet, or spray. Pills, tablets, suppositories, aerosols, powders, droplets, and sprays can have complex, multilayer structures and have a large range of sizes. Aerosols, powders, droplets, and sprays can range from small (1 micron) to large (200 micron) in size.

Pharmaceutical compositions disclosed herein can be used in the form of a solid, a lyophilized powder, a solution, an emulsion, a dispersion, and the like, wherein the resulting composition contains one or more of the compounds disclosed herein, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semi-solid, or liquid form. In addition, auxiliary, stabilizing, thickening and coloring agents and perfumes may be used. Examples of a stabilizing dry agent include triulose, preferably at concentrations of 0.1% or greater (See, e.g., U.S. Pat. No. 5,314,695). The active compound is included in the pharmaceutical composition in an amount sufficient to produce the desired effect upon the process or condition of diseases.

Most preferably, minicell-based biopharmaceuticals formulated for human use, especially parenteral use, should conform to sterility under U.S. Pharmacopeia <71>. The present disclosure includes by way of reference a method of sterilizing minicell preparations intended for use in humans by exposure to sterilizing doses of gamma irradiation. Such referenced methods are described in PCT/US2016/045400 and incorporated herein.

In some embodiments, a composition comprising the bacterial minicells and one or more immune checkpoint inhibitors is administered to a subject in need thereof. The composition comprising the bacterial minicells can also be co-administered to the subject with the one or more immune checkpoint inhibitors in separate compositions.

For example, some embodiments include administration of a first pharmaceutical composition comprising: (a) a safe and therapeutically effective amount of bacterial minicells, and (b) a pharmaceutically acceptable carrier, diluent, excipient or combination thereof; and a second pharmaceutical composition comprising: (a) one or more immune checkpoint inhibitors, and (b) a pharmaceutically acceptable carrier, diluent, excipient or combination thereof. In some embodiments, the first composition comprising the bacterial minicells and the second composition comprising one or more immune checkpoint inhibitors are administered to the subject simultaneously, for example accomplished by combing the first and second compositions in a single dosage form. The first composition and the second composition can be, in some embodiments, administered sequentially, through the same route (e.g., oral or intravenously), or through different route (e.g., one being administered orally and another being administered intravenously). In some embodiments, the first composition comprising the bacterial minicells is administered into the subject before the second composition comprising the one or more immune checkpoint inhibitors. In some embodiments, the first composition comprising the bacterial minicells is administered into the subject after the second composition comprising the one or more immune checkpoint inhibitors. The first composition, the second composition, or both can be administered to the subject more than once, for example twice, three times, four times, five times, six times, or more, for the treatment. In some embodiments, the first composition and the second composition are administered to the subject in alternate. For example, the subject can be administered with the first composition first, then the second composition, then the first composition, and then the second composition. In some embodiments, the subject is administered with the first composition only once, and then the second composition once, twice, three times, five times, six times, or more. In some embodiments, the subject is administered with the first composition no more than six times (for example, six times, five times, four times, three times, twice or once), and the second composition once, twice, three times, five times, six times, or more. The time period (i.e., the interval) between administration of the first composition and the second composition can vary, for example, be at least 1 minutes, 2 minutes, 5 minutes, 10 minutes, 30 minutes, 60 minutes, 2 hours, 6 hours, 12 hours, 18 hours, 1 day, 2 days, 3 days, 4 days, 5 days, 8 days, 10 days, 15 days, 20 days, 30 days, or more.

Administration of the pharmaceutical compositions described herein (for example, the compositions comprising the bacterial minicells, and the compositions comprising one or more immune checkpoint inhibitors) can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, intravesically, intraocularly, or by pleural or other (e.g. intracranial) infusion via stent. Oral, intravesical and parenteral administrations are customary in treating the indications that are the subject of the preferred embodiments.

In some embodiments, the methods described herein comprise administering one or more additional chemotherapeutic agents to the subject. At least one of the one or more additional chemotherapeutic agents can be administered to the subject separately from the composition comprising the bacterial minicells and/or the composition comprising the one or more immune checkpoint inhibitors.

Therapeutic Indications and Methods of Treatment

The present application relates to minicell-mediated or oncolytic minicell-mediated promotion of tumor-specific immune responses against cancer(s), especially CTL responses, against cancer types including but not limited to solid tumors, metastatic tumors, and liquid tumors. Solid and metastatic tumors include those of epithelial, fibroblast, muscle and bone origin and include but are not limited to breast, lung (including malignant pleural mesothelioma), pancreatic, prostatic, testicular, ovarian, gastric, intestinal, mouth, tongue, pharynx, hepatic, anal, rectal, colonic, esophageal, urinary bladder, gall bladder, skin, uterine, vaginal, penal, and renal cancers. Other solid cancer types that may be treated with the immunomodulatory minicells disclosed herein include but are not limited to adenocarcinomas, sarcomas, fibrosarcomas, and cancers of the eye, brain, and bone. Liquid tumors that can be treated by the minicells and oncolytic minicells disclosed herein include but are not limited to non-Hodgkin's lymphoma, myeloma, Hodgkin's lymphoma, acute lymphocytic leukemia, chronic lymphocytic leukemia, acute myeloid leukemia, chronic myeloid leukemia, and other leukemias.

Methods for treating cancer using the pharmaceutical compositions described herein to a subject in need thereof are disclosed herein. Some embodiments relate to a method for treating cancer, comprising co-administering bacterial minicells and one or more immune checkpoint inhibitor to a subject in need thereof. The subject can be a mammal, for example, a human.

Some embodiments relate to methods of activating immune response against cancer by co-administering bacterial minicells and one or more immune checkpoint inhibitors. Some embodiments relate to methods of stimulation of T-cell activation against cancer by co-administering bacterial minicells and one or more immune checkpoint inhibitors. Some embodiments relate to methods of stimulation of natural killer cells against cancer by co-administering bacterial minicells and one or more immune checkpoint inhibitors.

Various of cancers can be treated using the methods of combination therapy and compositions disclosed herein. For example, the cancer can be head and neck cancer, lung cancer, stomach cancer, colon cancer, pancreatic cancer, prostate cancer, breast cancer, kidney cancer, bladder cancer, ovary cancer, cervical cancer, melanoma, glioblastoma, myeloma, lymphoma, or leukemia. In some embodiments, the cancer is renal cell carcinoma, malignant melanoma, non-small cell lung cancer (NSCLC), ovarian cancer, Hodgkin's lymphoma or squamous cell carcinoma. In some embodiments, the cancer is selected from breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma. In some embodiments, the cancer is a solid tumor or hematological cancer. The cancer can be a solid tumor or hematological cancer.

In some embodiments, the treatment cycle can include co-administering minicells and one or more immune checkpoint inhibitors in combination with administering minicells alone or administering one or more checkpoint inhibitor alone. In some embodiments, minicells and one or more immune checkpoint inhibitor are co-administered on day 1, followed by administration of minicells alone after 1 day, 2 days, 3 days, 4 days, 5 days, 6 days, 7 days, 2 weeks, or 3 weeks, and then followed by co-administration of minicells and one or more immune checkpoint inhibitor after 1 day, 2 days, 3 days, 4 days, 5 days, 6 days, 7 days, 2 weeks, or 3 weeks. In some embodiments, minicells and one or more immune checkpoint inhibitor are administered simultaneously on day 1, followed by administration of minicells or one or more immune checkpoint inhibitor alone on a day selected between day 2 and day 31, and then followed by co-administration of minicells and one or more immune checkpoint inhibitor on a day selected between day 3 and day 31. In some embodiments, minicells and one or more immune checkpoint inhibitor are co-administered on day 1, followed by administration of minicells alone on day 8, and then followed by co-administration of minicells and one or more immune checkpoint inhibitor on day 15. In some embodiments, the treatment cycle can be repeated two or more times.

Disclosed here in are pharmaceutical compositions comprising bacterial minicells and/or one or more immune checkpoint inhibitors. In some embodiments, the composition further comprises one or more pharmaceutically acceptable excipients. In some embodiments, the composition further comprises one or more additional chemotherapeutic agents. In some embodiments, the composition comprises D-trehalose. Methods for treating cancer are also disclosed herein. In some embodiments, the method comprises administering any of the bacterial minicell-containing pharmaceutical compositions disclosed herein to a subject in need thereof. In some embodiments, the method comprises co-administering bacterial minicells and one or more immune checkpoint inhibitors to a subject in need thereof. In some embodiments, the method comprises administering a first pharmaceutical composition comprising bacterial minicells and a second pharmaceutical composition comprising one or more immune checkpoint inhibitors to a subject in need thereof. In some embodiments, the first pharmaceutical composition comprises D-trehalose. In some embodiments, the bacterial minicells comprise Invasin or a functional fragment thereof. In some embodiments, the bacterial minicells comprise perfringolysin O (PFO) or a functional fragment thereof. In some embodiments, the oncolytic minicell-based biopharmaceutical product is VAX014 (comprising VAX-IP). The types of immune checkpoint inhibitors used in combination with minicells can vary. In some embodiments, the one or more immune checkpoint inhibitors are inhibitors of PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, KIR, or a combination thereof. In some embodiments, the one or more immune checkpoint inhibitors are antibodies of PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, KIR, or a combination thereof. In some embodiments, the immune checkpoint inhibitor is nivolumab, pembrolizumab, pidilizumab, ipilimumab, BMS 936559, atezolizumab, durvalimumab, avelumab, or any combination(s) thereof.

Minicell Preparations

Some embodiments relate to creating an optimized strain and preparing immunomodulatory minicells from, but not limited to, the bacterial family Enterobacteriaceae.

In some embodiments, the level of minicell producing viable parental cell contamination is less than 1 in $10^5$ minicells. In some embodiments, the level of minicell producing viable parental cell contamination is less than 1 in $10^6$ minicells.

In some embodiments, the level of minicell producing viable parental cell contamination is less than 1 in $10^7$ minicells.

In some embodiments, the level of minicell producing viable parental cell contamination is less than 1 in $10^8$ minicells.

In some embodiments, the level of minicell producing viable parental cell contamination is less than 1 in $10^9$ minicells.

In some embodiments, the level of minicell producing viable parental cell contamination is less than 1 in $10^{10}$ minicells.

In some embodiments, the level of minicell producing viable parental cell contamination is less than 1 in $10^{11}$ minicells.

In some embodiments, the level of minicell producing viable parental cell contamination is less than 1 in $10^{12}$ minicells.

In some embodiments, the level of minicell producing viable parental cell contamination is less than 1 in $10^{13}$ minicells.

In some embodiments, the level of minicell producing viable parental cell contamination is less than 1 in $10^{14}$ minicells.

In some embodiments, the level of minicell producing viable parental cell contamination is less than 1 in $10^{15}$ minicells.

In some embodiments, the level of minicell producing viable parental cell contamination is less than 1 in $10^{16}$ minicells.

Unless defined otherwise, all technical and scientific terms used herein have the same meaning as commonly understood by one of ordinary skill in the art. Although the present application has been described with reference to embodiments and examples, it should be understood that various modifications can be made without departing from the spirit of the invention. All references cited herein are expressly incorporated herein by reference in their entirety.

Embodiments of the present application are disclosed in further detail in the following examples, which are not in any way intended to limit the scope of the present application.

EXAMPLES

Example 1

Fifty-four (54) female C57BL/6 mice aged 6-8 weeks were anesthetized with ketamine/xylazine via intraperitoneal injection, and their bladders transurethrally catheterized using a sterile 24-gauge flexible angiocatheter. Once catheterized, urine was removed via syringe so as not to affect electroconductivity and 2 separate tumor attachment sites made at the bladder wall by electrocauterization using a 2 second pulse of 5 W monopolar output from a Bovie electrocautery unit placed in contact with a platinum guidewire inserted through the catheter lumen and touching the bladder wall (performed at 2 sites by repositioning guidewire between pulses). Following cauterization, MB49 murine transitional cell carcinoma cells were inserted into the bladder ($10^5$ cells in 50 μL of DMEM) and catheters locked in place to prevent voiding and ensure tumor take. After a 1 hr tumor dwell time, catheters were removed and animals allowed to recover prior to randomization into the treatment groups described below. Intravesical (IVE) treatments with $1\times10^8$ VAX014 minicells were initiated 24 hours (early treatment) post-tumor installation and given transurethrally once weekly for 6 weeks thereafter (q7dx6), each with a 1 hr WE treatment dwell time in mice anesthetized via i.p. administration of ketamine/xylazine and catheterized as described above.

Treatment groups are as follows: (1) saline treated controls (n=24; WE; q7dx6), and (2) early WE treatment with 1×10⁸ VAX014 (n=30; WE, q7dx6). After 60 days of observation, nine (9) surviving mice from the treatment group were randomly selected and re-challenged with a second round of orthotopic MB49 tumors and observed for an additional 60 days without receiving treatment. Controls for the re-challenge phase included treatment/tumor-naïve mice implanted with orthotopic MB49 tumors (n=6). Kaplan-Meier survival curves were plotted over the 60-day observation period for the primary orthotopic phase and the significance of overall survival rate and median survival time analyzed for significance using the Log-rank test. The re-challenge phase overall survival rate and median survival time were also recorded for 60 days and curves analyzed for significance using the Log-rank test. Eighty-nine percent (89%, 8 of 9) of mice surviving the primary orthotopic bladder tumor phase due to WE VAX014 treatments were capable of rejecting a second round of orthotopic MB49 bladder tumors, despite receiving no further treatment. The results are shown in FIG. 1.

Example 2

Thirty-two (32) female C57BL/6 mice aged 6-8 weeks were anesthetized with ketamine/xylazine via intraperitoneal (IP) injection, and their bladders transurethrally catheterized using a sterile 24-gauge flexible angiocatheter. Once catheterized, urine was removed via syringe so as not to affect electroconductivity and 2 separate tumor attachment sites are made at the bladder wall by electrocauterization using a 2 second pulse of 5 W monopolar output from a Bovie electrocautery unit placed in contact with a platinum guidewire inserted through the catheter lumen and touching the bladder wall (performed at 2 sites by repositioning guidewire between pulses). Following cauterization, MB49 murine transitional cell carcinoma cells were inserted into the bladder (10⁵ cells in 50 µL of DMEM) and catheters locked in place to prevent voiding and ensure tumor take. After a 1 hour tumor dwell time, catheters were removed and animals allowed to recover prior to randomization into the treatment groups described below.

Figure 2:
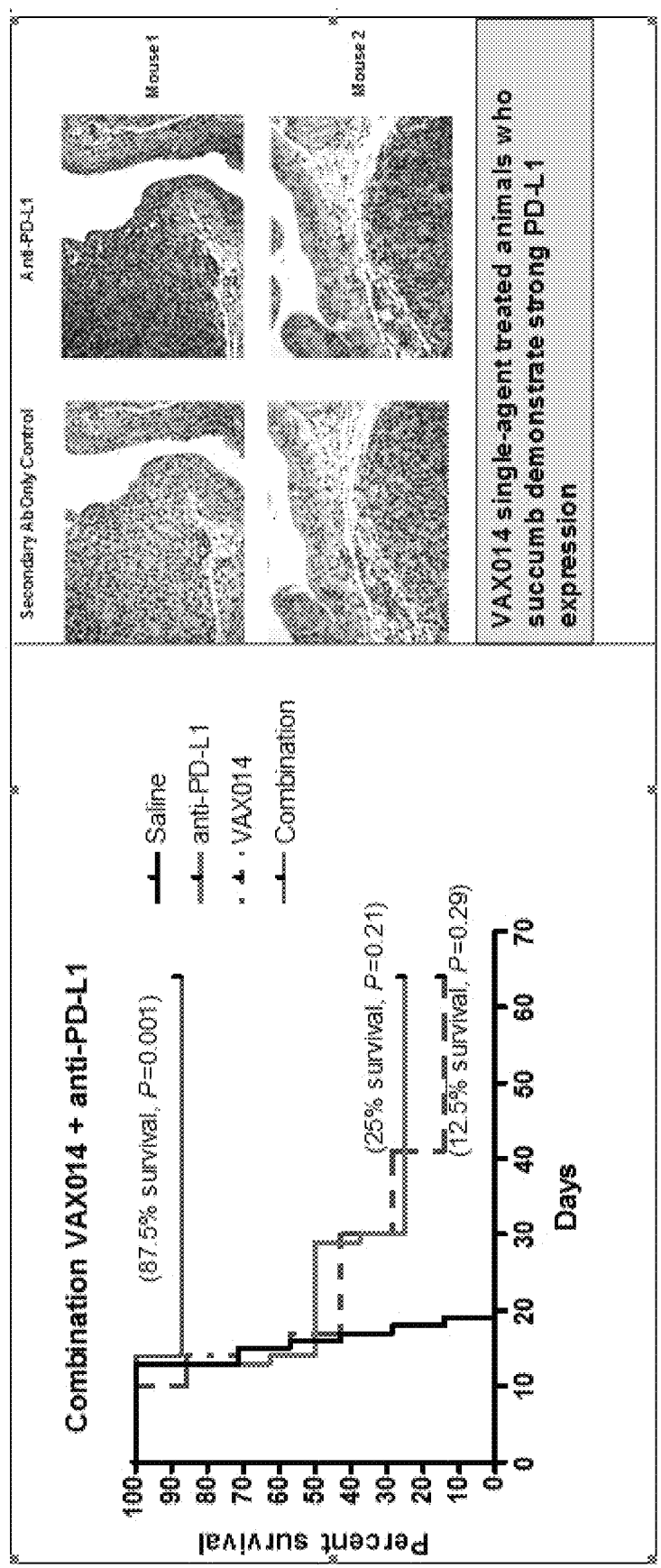
FIG. 2. Immune competent mice bearing well-established, large, digitally palpable orthotopic bladder tumors demonstrate complete tumor regression and survival with a combination therapy regimen consisting of IVE administration of oncolytic VAX014 minicells and systemic anti-PD-L1 therapy (~90% survival) versus either agent alone (<25% survival in each single agent control arm) or saline treated controls (0% survivors). Tumors from animals failing single-agent VAX014 each expressed high levels of PD-L1 as determined post mortem via immunohistochemistry.

Intravesical (IVE) treatments with VAX014 (1×10⁸ in 50 µL saline) were initiated on Day 7 post-tumor installation (late treatment of well-established digitally palpable orthotopic bladder tumors) and continued on a q7dx6 dosing schedule. Intraperitoneal (IP) administrations of anti-PD-L1 antibody (clone 10F.9G2) or an isotype control also began on Day 7 (dose of 200 µg in 100 µL) following IVE administration of VAX014 and continued from there on a q3dx5 schedule. Treatment groups (n=8/group) included (i) MB49, saline vehicle IVE q7dx6, saline; IP q3dx5 (ii) MB49, VAX014 IVE q7dx6+saline vehicle; IP q3dx5, (iii) MB49, saline vehicle IVE; q7dx6+anti-PD-L1 antibody (200 µg/dose); and (iv) IP q3dx5, and (iv) MB49, VAX014 IVE; q7dx6+anti-PD-L1 antibody (200 µg/dose). Animals were observed hourly post-dose for 6 hr, then observed and weighed every 2 days during the dosing phase and thereafter twice weekly for a total study time of 70 days. Kaplan-Meier survival curves were generated and analyzed for statistical significance using Log-rank test. The number of mice to be utilized in each group (n=8) was determined via Power Analysis, with Power set to 95%, α=0.05, and a historical tumor take rate of 100%, equaling 8/group to determine the statistical significance of treatment effect. The results are shown in FIG. 2.

Tumor-bearing bladders from mice bearing orthotopic MB49 tumors and failing IVE VAX014 single agent therapy were excised, fixed in paraformaldehyde, paraffin-embedded, sectioned and probed for PD-L1 expression via immunohistochemistry. All tumors from these animals exhibited high expression levels of PD-L1 (See FIG. 2).

Figure 3:
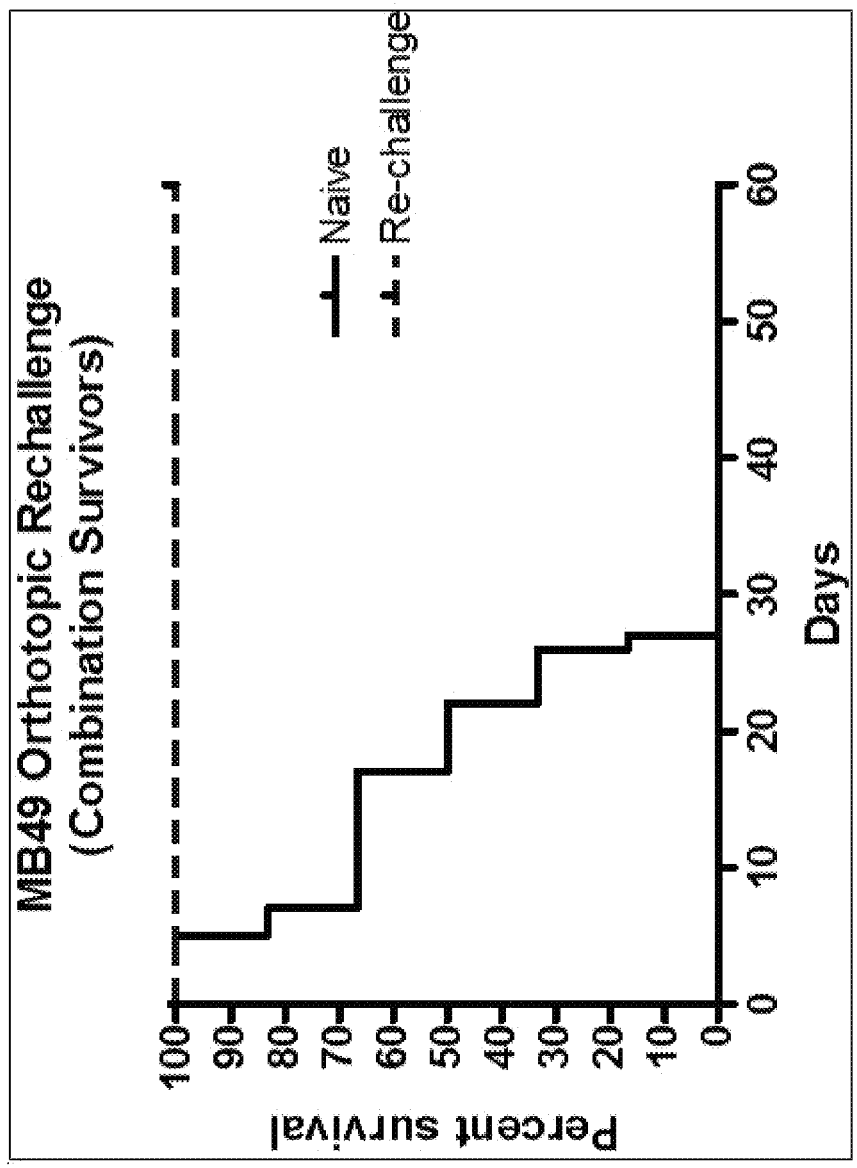
FIG. 3. Mice having complete orthotopic bladder tumor regression and surviving past in response to combination therapy with IVE VAX014 oncolytic minicells and systemic anti-PD-L1 therapy were capable of rejecting a second round of the same orthotopic bladder tumor type (100% rejected a second tumor installation).

Mice surviving 60 days following MB49 tumor installation and combination therapy consisting of IVE VAX014 and systemic anti-PD-L1 therapy (n=7 of 8 from FIG. 2) were re-challenged with a second round of orthotopic MB49 tumors and left untreated. Animals were observed hourly post-installation of tumors for 6 hr, then observed and weighed every 2 days for the first two weeks, and thereafter once weekly for a total re-challenge observation period of 60 days. Kaplan-Meier survival curves were generated and analyzed for statistical significance using Log-rank test. The results are shown in FIG. 3.

Similar experiments are repeated using different immune checkpoint inhibitors that include but are not limited to those against PD-1, CTLA-4, LAG-3, IDO, GITR, 4-1BB, OX40, CD27, KIR2DL, CSF1R, CD40L, and TIM-3. It is expected that the animals treated with both minicells and the immune checkpoint inhibitors have a higher survival rate or longer time to progression than the untreated animals or animals treated with either agent alone.

Example 3

Thirty (30) female C3H/HeN mice aged 6-8 weeks are anesthetized with ketamine/xylazine via intraperitoneal (IP) injection, and their bladders transurethrally catheterized using a sterile 24-gauge flexible angiocatheter. Once catheterized, urine is removed via syringe so as not to affect electroconductivity and 2 separate tumor attachment sites are made at the bladder wall by electrocauterization using a 2 second pulse of 5 W monopolar output from a Bovie electrocautery unit placed in contact with a platinum guidewire inserted through the catheter lumen and touching the bladder wall (performed at 2 sites by repositioning guidewire between pulses). Following cauterization, MBT-2 murine transitional cell carcinoma cells are inserted into the bladder (5×10⁵ cells in 50 µL of DMEM) and catheters locked in place to prevent voiding and ensure tumor take. After a 1 hr tumor dwell time, catheters are removed, and animals allowed to recover prior to randomization into the treatment groups described below.

Intravesical treatments with VAX014 (1×10⁸ in 50 µL saline) are initiated on a q7dx6 dosing schedule starting on Day 5 post-tumor installation. Intraperitoneal administrations of anti-PD-L1 antibody (clone 10F.9G2) or an isotype control also begin on Day 5 (dose of 200 µg in 100 µL) and continue on a q3dx5 schedule. Treatment groups (n=10/group) include (i) MBT-2, saline vehicle IVE, (ii) MBT-2, VAX014 IVE q7dx6+isotype control; IP q3dx5, and (iii) MBT-2, VAX014 IVE; q7dx6+anti-PD-L1 antibody; IP q3dx5. Animals are observed hourly post-dose for 6 hr, then observed and weighed every 2 days during the dosing phase and thereafter twice weekly for a total study time of 70 days. Kaplan-Meier survival curves are generated and analyzed for statistical significance using Log-rank test. The number of mice to be utilized in each group (n=10) was determined via Power Analysis, with Power set to 90%, α=0.01, and a historical tumor take rate of 90%, equaling 10/group to determine the statistical significance of treatment effect.

Experiments are repeated using different immune checkpoint inhibitors that include but are not limited to those against PD-1, CTLA-4, LAG-3, IDO, GITR, 4-1BB, OX40, CD27, KIR2DL, CSF1R, CD40L, and TIM-3. It is expected that the animals treated with both minicells and the immune checkpoint inhibitors have a higher survival rate or longer time to progression than the untreated animals or animals treated with either agent alone.

Example 4

Thirty (30) female C57BL/6 mice aged 6-8 weeks are anesthetized with ketamine/xylazine via intraperitoneal (IP) injection, and implanted subcutaneously with 1×10⁶ B16F10 murine melanoma cells in the subdermis of the right flank. Subcutaneous B16F10 tumor growth is monitored every other day by caliper measurement using the equation: tumor volume=0.5×length×width with until tumors reach a size of 100 mm³ at which point animals are randomized into treatment groups and treatment initiated.

Intravenous treatments with VAX014 (1×10⁸ in 100 µL saline) are initiated on a q3dx6 dosing schedule and intraperitoneal administrations of anti-PD-L1 antibody (clone 10F.9G2) or an isotype control also begin same day (dose of 200 µg in 100 µL) and continue on a q3dx5 schedule. Treatment groups (n=10/group) include (i) B16F10, saline vehicle IV, (ii) B16F10, VAX014 IV q3dx6+isotype control; IP q3dx5, and (iii) B16F10, VAX014 IV; q3dx6+anti-PD-L1 antibody; IP q3dx5. Animals are observed hourly post-dose for 2 hr, then observed and weighed every 2 days during the dosing phase and thereafter twice weekly for a total study time of 70 days. Kaplan-Meier survival curves are generated and analyzed for statistical significance using Log-rank test. In addition, during the in-life portion of the study, subcutaneous B16F10 tumor growth rate is monitored every other day by caliper measurement using the equation: tumor volume=0.5×length×width² with a subject termination endpoint at a tumor volume of 2000 mm³. The number of mice to be utilized in each group (n=10) was determined via Power Analysis, with Power set to 90%, $\alpha$=0.01, and a historical tumor take rate of 90%, equaling 10/group to determine the statistical significance of treatment effect.

Experiments are repeated using different immune checkpoint inhibitors that include but are not limited to those against PD-1, CTLA-4, LAG-3, IDO, GITR, 4-1BB, OX40, CD27, KIR2DL, CSF1R, CD40L, and TIM-3.

These experiments can also be repeated using other murine tumor cell lines syngeneic to the C57BL/6 mouse strain, including but not limited to Lewis Lung Carcinoma, and GL261. It is expected that the animals treated with both minicells and the immune checkpoint inhibitors have a higher survival rate or longer time to progression than the untreated animals or animals treated with either agent alone.

Example 5

Thirty (30) female Balb/c mice aged 6-8 weeks are anesthetized with ketamine/xylazine via intraperitoneal (IP) injection, and implanted subcutaneously with 1×10⁶ CT26 murine colorectal carcinoma cells in the subdermis of the right flank. Subcutaneous CT26 tumor growth is monitored every other day by caliper measurement using the equation: tumor volume=0.5×length×width² with until tumors reach a size of 100 mm³ at which point animals are randomized into treatment groups and treatment initiated.

Intravenous treatments with VAX014 (1×10⁸ in 100 µL saline) are initiated on a q3dx6 dosing schedule and intraperitoneal administrations of anti-PD-L1 antibody (clone 10F.9G2) or an isotype control also begin same day (dose of 200 µg in 100 µL) and continue on a q3dx5 schedule. Treatment groups (n=10/group) include (i) CT26, saline vehicle IV, (ii) CT26, VAX014 IV q3dx6+isotype control; IP q3dx5, and (iii) CT26, VAX014 IV; q3dx6+anti-PD-L1 antibody; IP q3dx5. Animals are observed hourly post-dose for 2 hr, then observed and weighed every 2 days during the dosing phase and thereafter twice weekly for a total study time of 70 days. Kaplan-Meier survival curves are generated and analyzed for statistical significance using Log-rank test. In addition, during the in-life portion of the study, subcutaneous CT26 tumor growth rate is monitored every other day by caliper measurement using the equation: tumor volume=0.5×length×width with a subject termination endpoint at a tumor volume of 2000 mm³. The number of mice to be utilized in each group (n=10) was determined via Power Analysis, with Power set to 90%, $\alpha$=0.01, and a historical tumor take rate of 90%, equaling 10/group to determine the statistical significance of treatment effect.

Experiments are repeated using different immune checkpoint inhibitors that include but are not limited to those against PD-1, CTLA-4, LAG-3, IDO, GITR, 4-1BB, OX40, CD27, KIR2DL, CSF1R, CD40L, and TIM-3.

These experiments can also be repeated using other murine tumor cell lines syngeneic to the Balb/c mouse strain, including but not limited to 4T1, RENCA, and MAD109. It is expected that the animals treated with both minicells and the immune checkpoint inhibitors have a higher survival rate or longer time to progression than the untreated animals or animals treated with either agent alone.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

In addition, where features or aspects of the disclosure are described in terms of Markush groups, those of ordinary skill in the art will recognize that the disclosure is also thereby described in terms of any individual member or subgroup of members of the Markush group.

As will be understood by one ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating cancer, comprising: administering a first pharmaceutical composition comprising bacterial minicells, wherein the first pharmaceutical composition comprises D-trehalose, and wherein the bacterial minicells comprise: invasin and perfringolysin O (PFO), and administering a second pharmaceutical composition comprising one or more immune checkpoint inhibitors to a subject with cancer, wherein the one or more immune checkpoint inhibitor is an antibody.

2. The method of claim 1, wherein the invasin is from *Yersinia pseudotuberculosis*.

3. The method of claim 1, wherein the first and second pharmaceutical compositions are administered to the subject simultaneously.

4. The method of claim 1, wherein the first and second pharmaceutical compositions are administered to the subject sequentially.

5. The method of claim 4, wherein the first pharmaceutical composition is administered to the subject before the second pharmaceutical composition is administered to the subject.

6. The method of claim 4, wherein the first pharmaceutical composition is administered to the subject after the second pharmaceutical composition is administered to the subject.

7. The method of claim 1, wherein the first pharmaceutical composition is administered to the subject via oral, intravenous, intraperitoneal, intragastric, intravesical administration, or a combination thereof.

8. The method of claim 1, wherein the second pharmaceutical composition is administered to the subject via oral, intravenous, intraperitoneal, intragastric, intravesical administration, or a combination thereof.

9. The method of claim 1, wherein the first pharmaceutical composition is administered to the subject at least twice.

10. The method of claim 1, wherein the second pharmaceutical composition is administered to the subject at least twice.

11. The method of claim 1, wherein the first and/or the second pharmaceutical composition comprises one or more pharmaceutically acceptable excipients.

12. The method of claim 1, further comprising administering one or more additional chemotherapeutic agents to the subject.

13. The method of claim 12, wherein at least one of the one or more additional chemotherapeutic agents is administered to the subject separately from the first and or the second compositions.

14. The method of claim 1, wherein the invasin is expressed on the surface of the bacterial minicells.

15. The method of claim 1, wherein the D-trehalose is present in an amount of about 12% (w/v).

16. The method of claim 1, wherein the bacterial minicells do not comprise any exogenous protein toxin other than PFO.

17. The method of claim 1, wherein the bacterial minicells do not comprise any exogenous therapeutic compounds or exogenous therapeutic protein other than PFO.

18. The method of claim 1, wherein the cancer is a solid tumor or hematological cancer.

19. The method of claim 1, wherein at least one of the one or more immune checkpoint inhibitors is selected from the group consisting of antibodies against PD-1, PD-L1, PD-L2, PD-L3, PD-L4, LAG-3, TIM-3, CTLA-4, B7-H3, B7-H4, IDO, GITR, 4-1BB, OX40, CD27, KIR2DL, CSF1R, CD40L, KIR, and any combinations thereof.

20. The method of claim 1, wherein the second pharmaceutical composition comprises anti-PD-L1 antibody.

* * * * *